US008586759B2

(12) United States Patent
Gryshuk et al.

(10) Patent No.: US 8,586,759 B2
(45) Date of Patent: Nov. 19, 2013

(54) METHODS AND SYSTEMS FOR SYNTHESIS OF A D-AMINOLUCIFERIN PRECURSOR AND RELATED COMPOUNDS

(75) Inventors: Amy L. Gryshuk, Livermore, CA (US); Julie Perkins, Sunnyvale, CA (US); John V. LaTour, Alameda, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 15 days.

(21) Appl. No.: 13/037,106

(22) Filed: Feb. 28, 2011

(65) Prior Publication Data

US 2011/0224442 A1 Sep. 15, 2011

Related U.S. Application Data

(60) Provisional application No. 61/308,317, filed on Feb. 26, 2010, provisional application No. 61/331,072, filed on May 4, 2010, provisional application No. 61/331,094, filed on May 4, 2010.

(51) Int. Cl.
*C07D 277/68* (2006.01)

(52) U.S. Cl.
USPC .......................................... 548/178

(58) Field of Classification Search
USPC .......................................... 548/178
See application file for complete search history.

(56) References Cited

U.S. PATENT DOCUMENTS

| | | | |
|---|---|---|---|
| 5,098,828 A | 3/1992 | Geiger et al. | |
| 7,101,694 B2 | 9/2006 | Hirokawa et al. | |
| 7,148,030 B2 | 12/2006 | O'Brien et al. | |
| 7,524,876 B2 | 4/2009 | Takakura et al. | |
| 2003/0211560 A1 | 11/2003 | O'Brien et al. | |
| 2004/0072178 A1 | 4/2004 | Hirokawa et al. | |
| 2006/0073529 A1 | 4/2006 | Contag et al. | |
| 2007/0155806 A1* | 7/2007 | Takakura et al. | 514/367 |
| 2011/0213124 A1 | 9/2011 | Gryshuk et al. | |
| 2011/0224442 A1 | 9/2011 | Gryshuk et al. | |

OTHER PUBLICATIONS

White et al., Journal of the American Chemical Society (1963), 85, pp. 337-343.*
O'Brien, M., et al., Homogeneous, Bioluminescent Protease Assays: Caspase-3 as a Model, The Soc. For Biomol. Screening 2005, 10: 137-148.
Lam, K., et al., The "One-Bead-One-Compound" Combinatorial Library Method, Chem. Rev. 1997, 97: 411-448.
Contag, C., et al., Photonic detection of bacterial pathogens in living hosts, Molecular Microbiology 1995, 18: 593-603.
De Angelis, G., et al. Twenty Years of PSA: From Prostate Antigen to Tumor Marker, Rev. Urol. 2007, 9: 113-123.
DeLuca, M., Firefly Luciferase, Advances in Enzymology and Related Areas of, 1976, 44: 37-68.
Denmeade, S., et al., Specific and Efficient Peptide Substrates for Assaying the Proteolytic Activity of Prostate-specific Antigen, Cancer Research 1997, 57: 4924-4930.
Hsieh, C.L., et al., Non-Invasive Bioluminescent Detection of Prostate Cancer Growth and Metastasis in a Bigenic Transgenic Mouse Mode, The Prostate 2007, 67: 685-691.
Huhtinen, P., et al., Immunoassay of total prostate-specific antigen using europium(III) nanoparticle labels and streptavidin—biotin technology, J. Immunol. Methods 2004, 294: 111-122.
Ignowski, J., et al., Kinetic Analysis and Modeling of Firefly Luciferase as a Quantitative Reporter Gene in Live Mammalian Cells, Biotech. and Bioeng. 2004, 86: 827-834.
Bernardi, R., et al., Nucleophilic Character of Carbon Free Radicals. A New Convenient, Selective Carboxyflation of Heteroaromatic Bases, Tetra. Let. 1973, 9: 645-648.
Sawhney, SN., et al., Benzothiazole Derivates: Part VIII—Synthesis of Some 2-(4-Alkyl or aryl-2-thiazolyl) benzothiazoles & 12-(4-Alkyl or aryl-2-thiazolylamino)-benzothiazoles as Potential Anti-inflammatory Agents, Indian Journal of Chemistry 1977, 15B: 121-124.
Theil, W., et al., Dithiocarbonsauren, Dithiocarbonsaureester oder Thiocarbonaureamide aus methylenaktiven Chlormethylverbindungen and Schwefel, J. F. prakt Chemie. 1989, 331: 243-262 (English abstract only).
Polshettlwar, V., et al., Thionation of carbonyl compounds using phosphorous pentasulfide and hexamethyldisiloxane under microwave irradiations, J. Chem. Res. 2004, 474-476.
Aso, Y., et al., Mild and Efficient Dehydrosulfurization of Thioamides to Nitriles induced by Tellurium or Selenium Tetrachoride with Triethylamine, J. Chem. Res. 1995, 1395: 152-153.
Jacobs, J., et al., Utilizing Human Blood Plasma for Proteomic Biomarker Discovery, J. Proteome Research 2005, 4: 1073-1085.
Katz, L., Antituberculous Compounds. 2-Benzalhydrazinobenzothiazoles, 1951: 4007-4010.
Koo, JY, et al., Bioluminescence of the firefly: Key steps in the formation of the electronically excited state for model systems, PNAS 1978, 75: 30-33.
Lee, K., et al., Noninvasive Molecular Imaging Sheds Light on the Synergy between 5-Fluorouracil and TRAIL/Apo2L for Cancer Therapy, Clinical Cancer Research 2007, 13: 1839-1846.
Lilja, H., et al., Prostate-specific antigen and prostate cancer: prediction, detection and monitoring, Nature Reviews Cancer 2008, 8: 268-278.
Mikolajczyk, S., et al., Are multiple markers the future of prostate cancer diagnostics?, Clinical Biochemistry 2004, 37: 519-528.
Monsees, T, et al., Synthesis and Characterization of a Bioluminogenic Substrate for α-Chymotrypsin, Analytical Biochemistry 1994: 221: 329-334.
Nagasaki, I., et al., Synthesis of Heteroarenenecarbonitriles by Electro-philic Cyanation; Reaction of Metalated Heteroarenes with p-Toluenesulfonyl Cyanide, Heterocycles 1997, 46: 443-450.
Niemela, P., et al., Sensitive and Specific Enzymatic Assay for the Determination of Precursor Forms of Prostatespecific Antigen after an Activation Step, Clinical Chemistry 2002, 1257-1264.
Cali, J., et al., P450-glo™ Cyp2c19 and cyp2d6 Assays and Screening Systems: The Method of Choice for In vitro p450 Assays, Cell Notes 2006, 14: 20-24.

(Continued)

*Primary Examiner* — Laura L. Stockton
(74) *Attorney, Agent, or Firm* — Steinfl & Bruno, LLP

(57) ABSTRACT

Methods and systems to generate 6-amino-6-deoxy-D-luciferin precursor, 2-cyano-6-aminobenzothiazole and related compounds and derivatives.

4 Claims, 33 Drawing Sheets

(56) References Cited

OTHER PUBLICATIONS

Reed, LJ, et al., A Simple Method of Estimating Fifty per Cent Endpoints, The American Journal of Hygienie 1938, 27: 493-497.

Seliger, HH, et al., Spectral Emission and Quantum Yield of Firefly Bioluminecence, Archives of Biochem. & Biophy. 1960, 88: 136-141.

Stenman, U., et al., Summary Report of the TD-3 Workshop: Characterization of 83 Antibodies against Prostate-Specific Antigen, Tumor Bioliogy 1999, 20(suppl.): 1-12.

White, E., et al., Amino Analogs of Firefly Luciferin and Biological Activity Thereof, J. Amer. Chem. Soc. 1966, 88: 2015-2019.

Suzuki, N., et al., Studies on Firefly Bioluminescence I, Tetrahedron. 1972, 28: 4065-4074.

Shinde, R., et al., Luciferin Derivatives for Enhanced in Vitro and in Vivo Bioluminescence Assays, Biochemistry 2006, 45: 11103-11112.

Finney, D, Assays based on quantal responses, Statistical method in biological assay, $3^{rd}$ edition, 1978, 371-403.

Etzioni, R., et al., The case for early detection, Nat. Rev. 2003, 3: 1-10.

Restriction Requirement mailed on Jan. 18, 2013 for U.S. Appl. No. 13/101,013, filed May 4, 2011 in the name of Christopher H. Contag et al.

Non-Final Office Action mailed on May 7, 2013 for U.S. Appl. No. 13/101,013, filed May 4, 2011 in the name of Christopher H. Contag et al.

Non-Final Office Action mailed on Jul. 18, 2013 for U.S. Appl. No. 13/037,163, filed Feb. 28, 2011 in the name of Amy L. Gryshuk et al.

White, E., et al., The Structure and Synthesis of Firefly Luciferin, J. American Chemical Society 1963, 85: 337-343.

\* cited by examiner

METHODS AND SYSTEMS FOR SYNTHESIS OF A D-AMINOLUCIFERIN PRECURSOR AND RELATED COMPOUNDS

CROSS REFERENCE TO RELATED APPLICATIONS

This application is related and claims priority to U.S. Provisional Application No. 61/308,317 entitled "Alternate Syntheses of Precursor to D-Aminoluciferin" filed on Feb. 26, 2010, to U.S. Provisional Application No. 61/331,072 entitled "Bioluminescent Protease Probe For The Detection Of Disease" filed on, May 4, 2010 with and to U.S. Provisional Application No. 61/331,094 entitled "Carboxylate-Modified Luciferin, Amino Acid/Peptide Probes For Bioluminescent Protease Assays" filed on, May 4, 2010 with each of which is incorporated herein by reference in its entirety.

STATEMENT OF GOVERNMENT INTEREST

The United States Government has rights in this invention pursuant to Contract No. DE-AC52-07NA27344 between the United States Department of Energy and Lawrence Livermore National Security, LLC for the operation of Lawrence Livermore National Laboratory

FIELD

The present disclosure relates to bioluminescence and in particular to methods and systems for the synthesis of D-aminoluciferin precursor and related compounds.

BACKGROUND

Bioluminescence provides a useful read out for the detection of reactions in a background of optically complex materials such as cells and tissues and the signal-to-noise ratio can be very high.

Luciferases are enzymes that generate visible light through the oxidation of a specific substrate in the presence of oxygen and usually a source of energy (such as $Mg2^+$ and ATP). The reaction between firefly luciferase and the substrate luciferin, yields oxyluciferin, carbon dioxide and visible light with a maximum around 560 nm and with other wavelengths of light output identifiable by a skilled person.

For these reasons, bioluminescence and in particular luciferin and related compounds are routinely used for in vivo imaging applications and for additional techniques for in vitro and/or in vivo detection of targets and/or reactions.

SUMMARY

Provided herein are methods and systems to synthesize a precursor of D-aminoluciferin and related compounds and methods that in several embodiments allow to minimize mixture of products evident in the early steps and/or to conjugate D-aminoluciferin to amino acids and peptide sequences to generate probes suitable for bioluminescence assays.

According to a first aspect, a method and system to provide 2-cyano 6-amino-benzothiazole from a monofunctional benzothiazole is described. The method comprises providing a monofunctional benzothiazole attaching in position C2 a functional group of formula (I) ($C(=X_1)NH_2$) wherein $X_1$ is O or S, and converting the functional group of formula (I) to a cyanide group, through elimination of $H_2X_1$ from the monofunctional benzothiazole. In the method the monofunctional benzothiazole either comprises an amino group in position C6 or is modified to comprise an amino group in position C6. The system comprises one or more monofunctional benzothiazoles attaching in position C2 a functional group of formula (I), together suitable reagents for simultaneous combined or sequential use in the method to provide 2-cyano-6-aminobenzothiazole herein described According to a second aspect, a method and system to provide 2-cyano-6-aminobenzothiazole from a monofunctional benzothiazole is described. The method comprises providing a monofunctional benzothiazole attaching in position C2 a functional group of formula (II) ($C(=X_1)X_2R$) wherein R is an alkyl group, or a halogen atom; and $X_1$ and $X_2$ are independently O or S. The method also comprises converting the functional group of formula (II) into an amide of formula (I) ($C(=X_1)NH_2$) and converting the functional group of formula (I) to a cyanide group through elimination of a $H_2X_1$ from the monofunctional benzothiazole. In the method the monofunctional benzothiazole either comprises an amino group in position C6 or is modified to comprise an amino group in position C6. The system comprises at least two of one or more monofunctional benzothiazole attaching in position C2 a functional group of formula (I), and/or one or more monofunctional benzothiazole attaching in position C2 a functional group of formula (II) together suitable reagents for simultaneous combined or sequential use in the method to provide 2-cyano-6-aminobenzothiazole herein described.

According to a third aspect, a method and system to provide an amino acid labeled with 6-amino-6-deoxy-D-luciferin and amino acid obtainable thereby, are described. The method comprises conjugating the amino acid with a 2-cyano-6-aminobenzothiazole to provide an amino acid-conjugated 2-cyano-6-aminobenzothiazole or 2-cyano-6-aminobenzothiazole-[amino acid, the conjugating performed to allow formation of a peptide bond, a carbamate bond or a urea/thiourea bond between the amino group of 6-amino-6-deoxy-D-luciferin and a carboxylic group of the amino acid. The method further comprises reacting the 2-cyano-6-aminobenzothiazole-[amino acid] with a D-cysteine to provide an amino acid-conjugated 6-amino-6-deoxy-D-luciferin. In the method, the amino acid is an amino acid having a side chain. The system comprises at least two of one or more amino acids with each amino acid having a side chain an amino acid-conjugated 2-cyano-6-aminobenzothiazole-[amino acid] and an amino acid-conjugated 2-cyano-6-aminobenzothiazole-[amino acid] for simultaneous combined or sequential use in the method to provide an amino acid labeled with 6-amino-6-deoxy-D-luciferin herein described.

According to a fourth aspect, an intermediate in the synthesis of an amino acid labeled with 6-amino-6-deoxy-D-luciferin is described. The intermediate is a 2-cyano-6-aminobenzothiazole of formula (III)

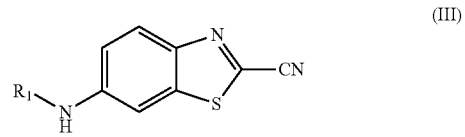

(III)

wherein R1 is an amino acid attached to the remainder of the compound of formula (III) through a peptide bond, a carbamate bond or a urea/thiourea bond.

According to a fifth aspect, a method and system to provide a peptide labeled with 6-amino-6-deoxy-D-luciferin is described. The method comprises conjugating the peptide with an amino acid-conjugated 2-cyano-6-aminobenzothiazole to provide a peptide-conjugated 2-cyano-6-aminobenzothiazole, the conjugating performed to allow formation of a peptide bond between the amino group of the amino acid-conjugated 2-cyano-6-aminobenzothiazole and a carboxylic acid group of the peptide. The method can further comprise reacting the peptide-conjugated 2-cyano-6-aminobenzothiazole with D-cysteine to provide a peptide-conjugated 6-amino-6-deoxy-D-luciferin. The system comprises one or more peptides, amino acids, 2-cyano-6-aminobenzothiazole, 2-cyano-6-amino-aminoacid-benzothiazoles and/or 2-cyano-6-amino-peptide-benzothiazoles for simultaneous combined or sequential use in the method to provide a peptide labeled with 6-amino-6-deoxy-D-luciferin herein described.

According to a sixth aspect, an intermediate in the synthesis of a peptide labeled with 6-amino-6-deoxy-D-luciferin is described. The intermediate is a 2-cyano-6-aminobenzothiazole of formula (IV)

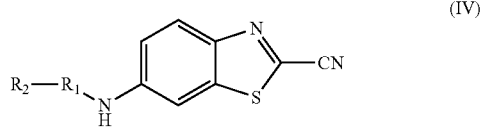

(IV)

wherein R1 is a single amino acid and R2 is a peptide attached to the remainder of the compound of formula (IV) through a peptide bond a carbamate bond or a urea/thiourea bond.

According to a seventh aspect, a labeled peptide is described. The labeled peptide is obtainable by the method to provide a peptide conjugated to 6-amino-6-deoxy-D-luciferin herein described.

According to an eighth aspect, a carboxylate-modified luciferin amino acid/peptide probe, is described and related method for synthesis and/or use of said carboxylate modified probe. The carboxylate-modified D-luciferin, amino acid/peptide probe comprises a D-luciferin molecule conjugated to an amino acid or peptide wherein conjugation between the D-luciferin and the amino acid or peptide is performed with peptide bond between the amino-terminus of the amino acid or peptide and a carboxyl group of the said D-luciferin.

The methods and systems described allow in several embodiments facilitating the generation of amounts of pure 6-amino-6-deoxy-D-luciferin (D-aminoluciferin) precursor.

The methods and systems described allow in several embodiments facilitating the coupling of 6-amino-6-deoxy-D-luciferin (D-aminoluciferin) precursor to peptide sequences and/or to single amino acids in solution phase.

The methods and systems described allow in several embodiments generation of pure 6-amino-6-deoxy-D-luciferin (D-aminoluciferin) precursor and/or subsequent coupling to peptide sequences and/or to single amino acids in a solution phase.

The methods and systems described herein can be used in connection with applications wherein production of D-aminoluciferin and/or related uses and/or derivatives is desired, including but not limited to medical application, biological analysis and diagnostics including but not limited to clinical applications.

The details of one or more embodiments of the disclosure are set forth in the accompanying drawings and the description below. Other features, objects, and advantages will be apparent from the description and drawings, and from the claims.

BRIEF DESCRIPTION OF THE DRAWINGS

The accompanying drawings, which are incorporated into and constitute a part of this specification, illustrate one or more embodiments of the present disclosure and, together with the detailed description and the examples, serve to explain the principles and implementations of the disclosure.

FIG. 4 shows nuclear magnetic resonance spectra for compounds of methods and systems of the disclosure, according to an embodiment herein described.

FIG. 8 shows a nuclear magnetic resonance ($^{13}$C-NMR) spectra of ethyl 6-nitrobenzothiazole-2-carboxylate 7 obtained on a Bruker 500 MHz machine in $d_6$-DMSO.

FIG. 10 shows a schematic representation of the two steps depicted in FIG. 9 according to an embodiment herein described. In particular.

FIG. 16-1, 16-2, and 16-3 show liquid chromatography/mass spectrometry spectra for compounds of methods and systems of the disclosure, according to an embodiment herein described.

DETAILED DESCRIPTION

Provided herein are methods and systems to synthesize a precursor of 6-amino-6-deoxy-D-luciferin, (herein also D-aminoluciferin), and derivatives thereof, which can be used in connection with various applications that are based on the reaction between luciferase enzyme of the North American firefly (*Photinus pyralis*) and substrate D-luciferin.

The reaction between the luciferase enzyme and substrate D-luciferin is widely used as an optical reporter for in vitro and in vivo assays. Broad ranging applications of the luciferase enzyme as optical reporter comprise reporting gene expression[1], proliferation of cancerous cells,[2] efficacy of cancer therapies[3], bacterial infection[4] and enzymatic action.[5,6] Under various reaction conditions identifiable by a skilled person, photons are generated during the enzymatic conversion of D-luciferin to oxyluciferin in the presence of compounds such as ATP, $O_2$ and $Mg^{2+}$.[7-9] In several cases bioluminescence can be detected with a low intrinsic background in cells and tissues, sometimes in contrast to fluorescent-based detection, where autofluorescence emits significant background noise. Studies to modify the natural substrate D-luciferin in numerous positions have generated substrates with novel properties. For example, masking the carboxyl group and/or methylating the 6-position phenolic group of D-luciferin inhibits reaction with the luciferase enzyme. Enzymatic or chemical hydrolysis of the carboxylic acid mask and demethylation of the methoxy group releases the free substrate for subsequent reaction with the luciferase enzyme.[6] In various cases 6-amino-6-deoxy-D-luciferin, D-aminoluciferin, with an amino group in the 6-position on the benzothiazole ring,[10] allows conjugation of the optical reporter substrate to peptide sequences to generate protease assay probes.[5,10,11-13]

Figure 1:
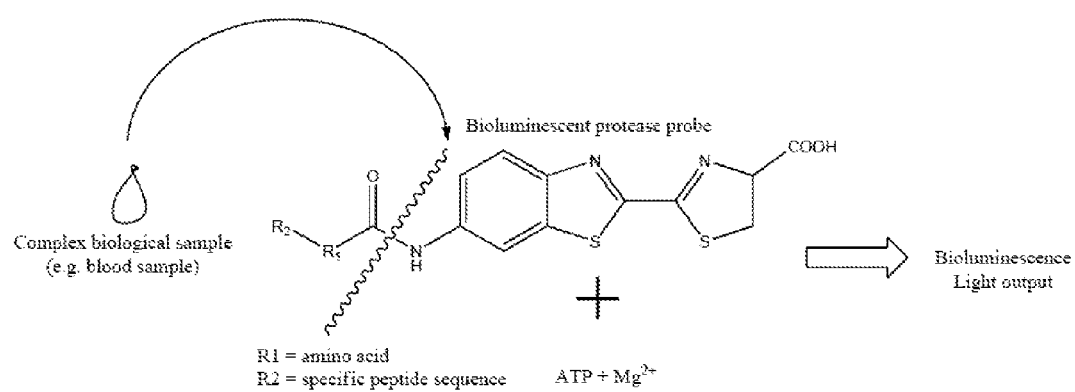
FIG. 1 shows a schematic representation of a bioluminescent assay based on release of D-aminoluciferin from labeled compounds according to an embodiment herein described.

FIG. 1 shows a cartoon scheme depicting an exemplary application of bioluminescent assay performed with labeled probes obtainable with the methods and systems herein described. In particular, in the illustration of FIG. 1, a complex biological sample (ex. blood sample) when interacting with a specifically designed protease probe has the capability to release the D-aminoluciferin, which ultimately provides light output in the presence of $Mg^{2+}$ and ATP when proteases (e.g. indicative of disease) are present in the biological sample. In some embodiments, this assay can serve as a marker for disease.

Methods and systems are herein described to provide a D-aminoluciferin precursor formed by 2-cyano-6-aminobenzothiazole (herein also D-aminoluciferin precursor or simply precursor) and/or probes labeled with D-aminoluciferin provided starting from the precursor.

In some embodiments, methods and systems are described to provide the precursor with method starting from a monofunctional benzothiazole. The term "benzothiazole" as used herein indicates an organosulfur compound of formula (V)

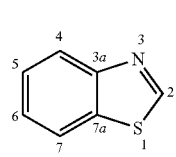

(V)

which can be substituted or unsubstituted in the various positions. Benzothiazole is typically colorless, and takes the form of a slightly viscous liquid while most of its derivatives are solid. Benzothiazoles are commercially available and can be prepared using methods such as treatment of 2-aminobenzenethiol with acid chlorides according to the reaction $C_6H_4(NH_2)SH+RC(O)Cl \rightarrow C_6H_4(NH)SCR+HCl+H_2O$ and to additional procedures identifiable by a skilled person.

The term "monofunctional benzothiazole" indicates a benzothiazole including one functional group in the C2 position wherein the term "functional group" as used herein indicates a specific group of atoms within a molecular structure that are responsible for the characteristic chemical interactions or reactions of that structure. In general, exemplary functional groups include hydrocarbons, groups containing halogen, groups containing oxygen, groups containing nitrogen and groups containing sulfur all identifiable by a skilled person. In particular, exemplary functional groups in the sense of the present disclosure comprise alkoxy or alkyl groups, secondary amines, amides and additional functional groups can be identified by a skilled person upon reading of the present disclosure. In some embodiments, the monofunctional benzothiazole can be substituted in any positions, wherein the terms "substituted" or "substitution" herein indicates replacement of one or more hydrogens with chemical groups that do not substantially interfere with the characteristic chemical interactions or reactions of the functional group as described herein.

In some embodiments, methods and systems are described to provide the precursor with methods starting from a monofunctional benzothiazole attaching in position C2 a functional group of formula (I) $(C(=X_1)NH_2)$ wherein $X_1$ is O or S, wherein the amide in the functional group of formula (I) is converted to a cyanide group by elimination of a $H_2X_1$ compound.

The term "amide" as used herein indicates an organic compound that contains the carbonyl group ($R_4$—C=O) linked to a nitrogen atom (N) (herein also carboxamide) or a thioamide group $R_4$—CS—NR'$R_5$, where $R_4$, R', and $R_5$ are same or different and are organic groups with R' and $R_5$ possibly formed by H. The term refers both to a class of compounds and a functional group within those compounds.

In particular, the term "carboxamide" as used herein indicates an organic compound that contains a carbonyl group (R4—C=O) linked to a nitrogen atom (N). Typically, carboxamides of the general structure R6—CO—NR7R2R8 can be synthesized by replacement of the hydroxyl group (OH) of a carboxylic acid by an amino group (NR1R2), where R6, R7, and R8 are same or different and are organic substituents with R7 and R8 possibly formed by H. Exemplary compounds containing carboxamide groups comprise asparagine and glutamine.

The term thioamides indicates sulfur analogues to amides, where the oxygen atom (O) in amide is replaced by a sulfur atom (S). The general structure of thioamide is $R_4$—CS—NR'$R_5$, where $R_4$, R', and $R_5$ are same or different and are organic groups with R' and $R_5$ possibly formed by H. Typically thioamides are analogous to carboxamides but they exhibit greater multiple bond character along the C—N bond, resulting in a larger rotational barrier. Thioamides are typically prepared by treating amides with phosphorus sulfides such as phosphorus pentasulfide and, in more specialized applications, Lawesson's reagent. An alternative route entails the reaction of nitriles with hydrogen sulfide. The Willgerodt-Kindler reaction also affords benzylthioamides.

The terms "eliminate" and "elimination reaction" as used herein with reference to a reaction indicate an elimination reaction. An elimination reaction is a type of organic reaction in which two substituents are removed from a molecule in either a one or two-step mechanism (E2 and E1 mechanisms, respectively). Either the unsaturation of the molecule increases or the valence of an atom in the molecule decreases by two. E1 mechanism: generally follows the following form: the first step requires the loss of the leaving group, forming a carbocation intermediate. A nucleophilic species, usually a base, then attacks a neighboring hydrogen forming the double bond. E2 mechanism generally follows the following form: a nucleophilic species or base attacks a hydrogen neighboring the leaving group, pushing the electrons into the double bond as the leaving group leaves. In elimination reactions herein described does not necessarily result in an actual production of an $H_2X_1$ product, as long as the $H_2X_1$ compound is removed from the starting compound. In this connection for example, in embodiments where $X_1$ is oxygen and a $POCl_3$ reagent is used the oxygen atom is eventually attached to phosphorus. Exemplary elimination reactions comprise dehydration and dehydrosulfurization. A dehydration reaction is usually defined as a chemical reaction that involves the loss of water from the reacting molecule. Dehydration reactions are a subset of elimination reactions where the leaving group is water ($H_2O$). Dehydrosulfurization reactions or $H_2S$ elimination reactions are another subset of elimination reaction where the leaving group is ($H_2S$).

In some embodiments, in the functional group of formula (I) $X_1$ is S, the conversion from thioamide to CN group can be performed by dehydrosulfurization directed to elimination the $H_2S$ compound. The dehydrosulfurization can be performed with suitable reagents (e.g. tellurium chloride) and under suitable conditions, such as the ones described for example in ref. 17. A skilled person will be able to identify additional reactions and related procedures that are functional to the dehydrosulfurization of the monofunctional benzothiazole herein described.

In some embodiments, in the functional group of formula (I) $X_1$ is O the reduction can be performed by dehydration of the corresponding ester group with production of $H_2O$ according to procedures such as the ones exemplified in the Examples section and additional procedures identifiable by a skilled person.

In some embodiments, the benzothiazole presenting the functional group of formula (I) in position C2 and/or the benzothiazole presenting the functional group CN comprises an amino group in position C6. In some embodiments, the benzothiazole presenting the functional group of formula (I) in position C2 is modified to comprise an amino group in position C6. In particular in some of those embodiments, a nitrile group is first introduced in position C6 before or after converting the functional group of formula (I) to a CN group. The nitrile group in C6 of the benzothiazole is then converted to an amino group. A skilled person will be able to identify suitable methods to introduce an NO2 group in monofunctional benzothiazoles herein described at any stage of the procedures. For example, typical nitrations use nitric acid and sulfuric acid to produces the nitronium ion ($NO_2^+$), which is the active species of nitration reactions and attacks the electron-rich reactant, such as a benzene ring, to initiate electrophilic substitution reaction.

In some embodiments, an NH2 is introduced directly into the C6 position of the benzothiazole ring. A skilled reader will be able to identify suitable reaction for introducing an NH2 group directly in monofunctional benzothiazoles herein described at any stage of the procedures herein described.

In some embodiments, the functional group of formula (I) can be provided in the monofunctional benzothiazole herein described starting from a monofunctional benzothiazole attaching in position C2 a functional group of formula (II) (C(=$X_1$)$X_2$R) wherein R is an alkyl group, or a halogen atom and $X_1$ and $X_2$ are independently O or S.

The term "alkyl" as used herein refers to a linear, branched, or cyclic saturated hydrocarbon group typically although not necessarily containing 1 to about 10 carbon atoms, preferably 1 to about 6 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although again not necessarily, alkyl groups herein contain 1 to about 6 carbon atoms. The term "cycloalkyl" intends a cyclic alkyl group, typically having 4 to 8, preferably 5 to 7, carbon atoms. The term "substituted alkyl" refers to alkyl substituted with one or more substituent groups, and the terms "heteroatom-containing alkyl" and "heteroalkyl" refer to alkyl in which at least one carbon atom is replaced with a heteroatom. If not otherwise indicated, the terms "alkyl" and "lower alkyl" include linear, branched, cyclic, unsubstituted, and/or substituted. In some embodiments, in the functional group of formula (I), R can be a substituted alkyl which can comprise heteroatoms such as N, O, S, P, Si, F, Cl, Br, and I, as well as additional groups and heteroatoms identifiable by a skilled person.

In embodiments where $X_2$ is O, the resulting $X_2$-R group can be an alkoxy group or an acid halide. The term "alkoxy" as used herein intends an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms. Exemplary alkoxy group comprised in the functional group of formula (I) comprise methoxy, ethoxy, propoxy and additional alkoxy group comprising a lower alkyl. The term "acid halide" indicates a chemical compound that can be typically derived from an oxoacid by replacing a hydroxyl group with a halide group (i.e. a binary compound, of which one part is a halogen atom and the other part is an element or radical that is less electronegative (or more electropositive) than the halogen). Exemplary acid halides comprise (C(=O)Cl) and additional halides identifiable by a skilled person. In some embodiments, the acyl halide can be treated with ammonia, and the reaction is expected to proceed faster than the reaction performed with the ester group.

In embodiments where $X_2$ is S the resulting $X_2$-R group is an alkyl group and in particular a lower alkyl group, or a halogen such as Cl. Exemplary functional groups of formula (II) comprise (C(=S)OR), which can be made for example by treating the ester with $P_2S_5$ as described in ref. 19; (C(=O)SR) which can be made for example by reacting the ester with a mercaptan under basic conditions as identifiable by a skilled person; and (C(=S)SR), which can be made for example by treating the chloromethylbenzothiazole with sulfur and methyl iodide, according to the procedure described in ref. 20. A skilled reader will be able to identify additional functional groups of formula (II) and suitable procedure to provide monofunctional benzothiazole comprising those functional groups.

In some embodiments, wherein the functional group of formula (I) and (II) $X_1$ is S, the conversion from ester to thioamide can be performed using reagents and procedures identifiable by a skilled person. For the conversion from ester to thioamide can be performed by using $NH_3$, then $P_2S_5$ as described in ref 18. Additional reactions will be identifiable by a skilled person upon reading of the present disclosure.

In some embodiments, wherein the functional group of formula (I) and (II) $X_1$ is O, the conversion from ester to carboxamide can be performed by using amines alone or in presence of reagents (such as dicyclohexylcarbodiimide (DCC)) which are suitable to convert the hydroxyl oxygen in a more efficient leaving group. Examples of those conversions are reported in the Example section of the present disclosure. A skilled reader will be able to identify additional reactions using amines or other reagents that are suitable to convert an ester according to formula (I) wherein $X_1$ is oxygen into a carboxamide of formula (II) wherein $X_1$ is oxygen.

Figure 2:
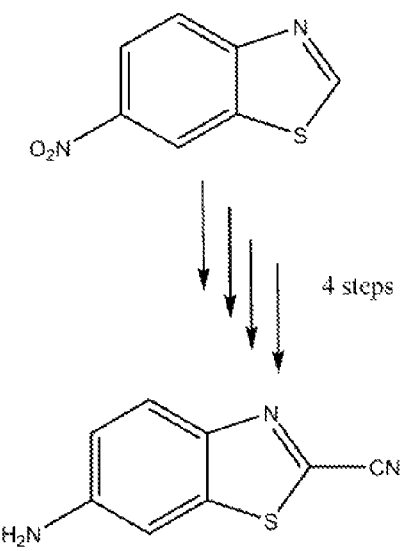
FIG. 2 shows a schematic representation of a method to provide 6-amino-2-cyanobenzothiazole from a monofunctional benzothiazole according to an embodiment herein described. In particular, the schematic of FIG. 2 illustrates a synthetic route of a 4 step process to generate D-aminoluciferin precursor, 2-cyano-6-aminobenzothiazole beginning with a monofunctional benzothiazole (6-nitrobenzothiazole).

In some embodiments of methods and systems wherein the D-aminoluciferin precursor is provided from a monofunctional benzothiazole, the monofunctional benzothiazole is 6-nitrobenzothiazole and the precursor can be synthesized according to a method schematically illustrated in FIG. 2. In particular, in the illustration of FIG. 2 production of the precursor can be performed in four steps. In particular a thio or carboxy ester functional group of formula (II) can be introduced in C2 with suitable reactions. The thio or carboxy ester can then be converted into a corresponding amide which can then be converted into a nitrile. The NO2 group in C6 can then be reduced to NH2 using procedure identifiable by a skilled person. Possible variations of this reaction scheme comprise a three steps procedure performed starting from a monofunctional benzothiazole attaching an ester of formula (II), three steps procedure performed starting from a monofunctional benzothiazole attaching an amide of formula (I) and other variations wherein the reduction of the NO2 group in C6 is performed before the final reduction of the amide of formula (I) to a CN group.

Figure 3:
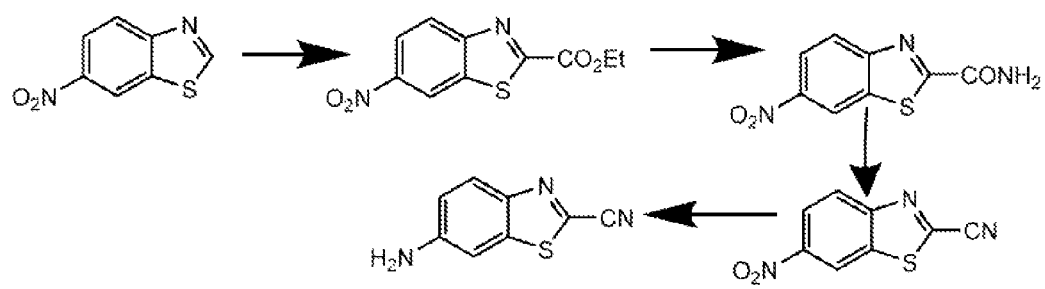
FIG. 3 shows a schematic representation of the four steps depicted in FIG. 2 according to an embodiment herein described. In particular, the schematic of FIG. 3 shows a specific route where a carboxyethyl functional group is introduced in the position C2 of 6-nitrobenzothiazole and then converted to a carboxamide group and on to a cyano group. The nitro group in position C6 of the resulting 2-cyano-6-nitrobenzothiazole is then reduced to an amino group.
Figure 4A:
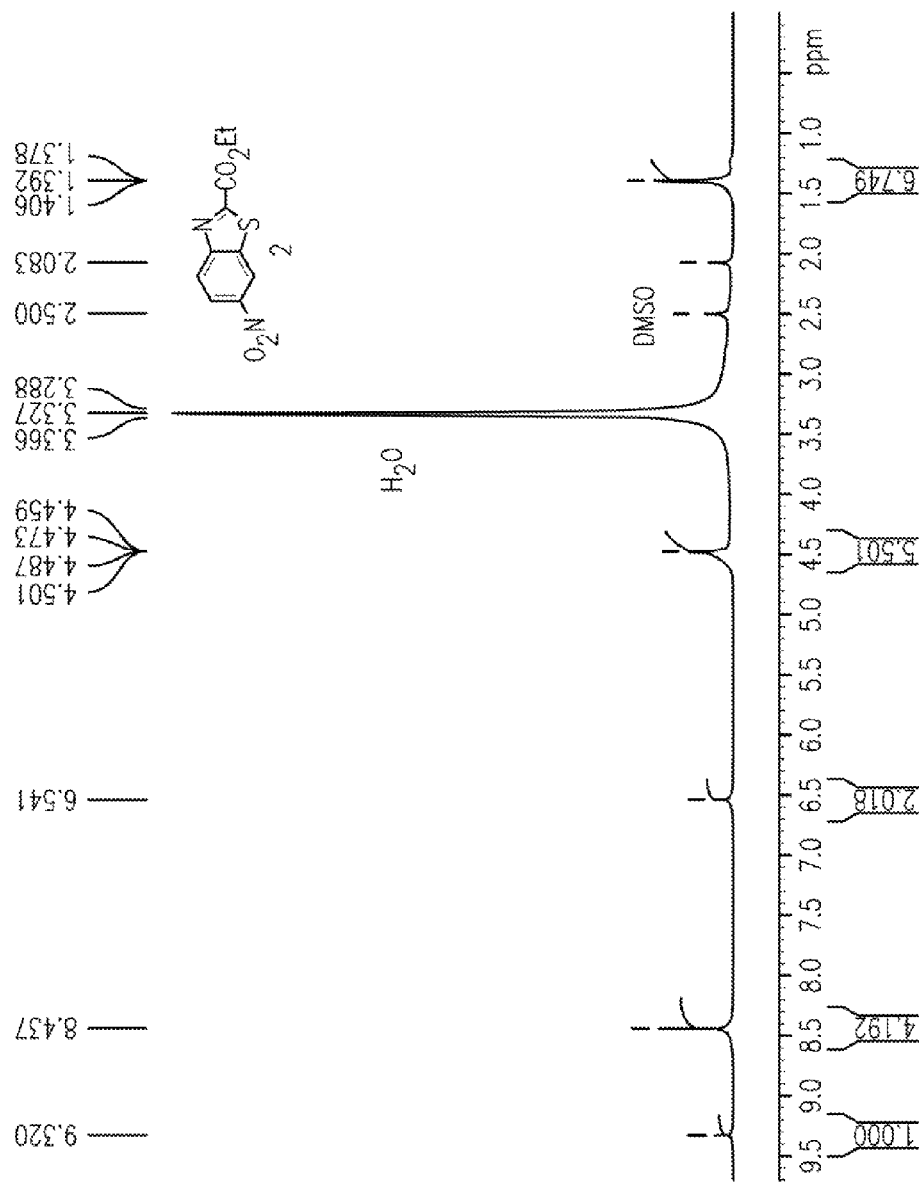
FIG. 4A shows a nuclear magnetic resonance ($^1$H-NMR) spectra of ethyl 6-nitrobenzothiazole-2-carboxylate 2 obtained on a Bruker 500 MHz machine in $d_6$-DMSO.
Figure 4B:
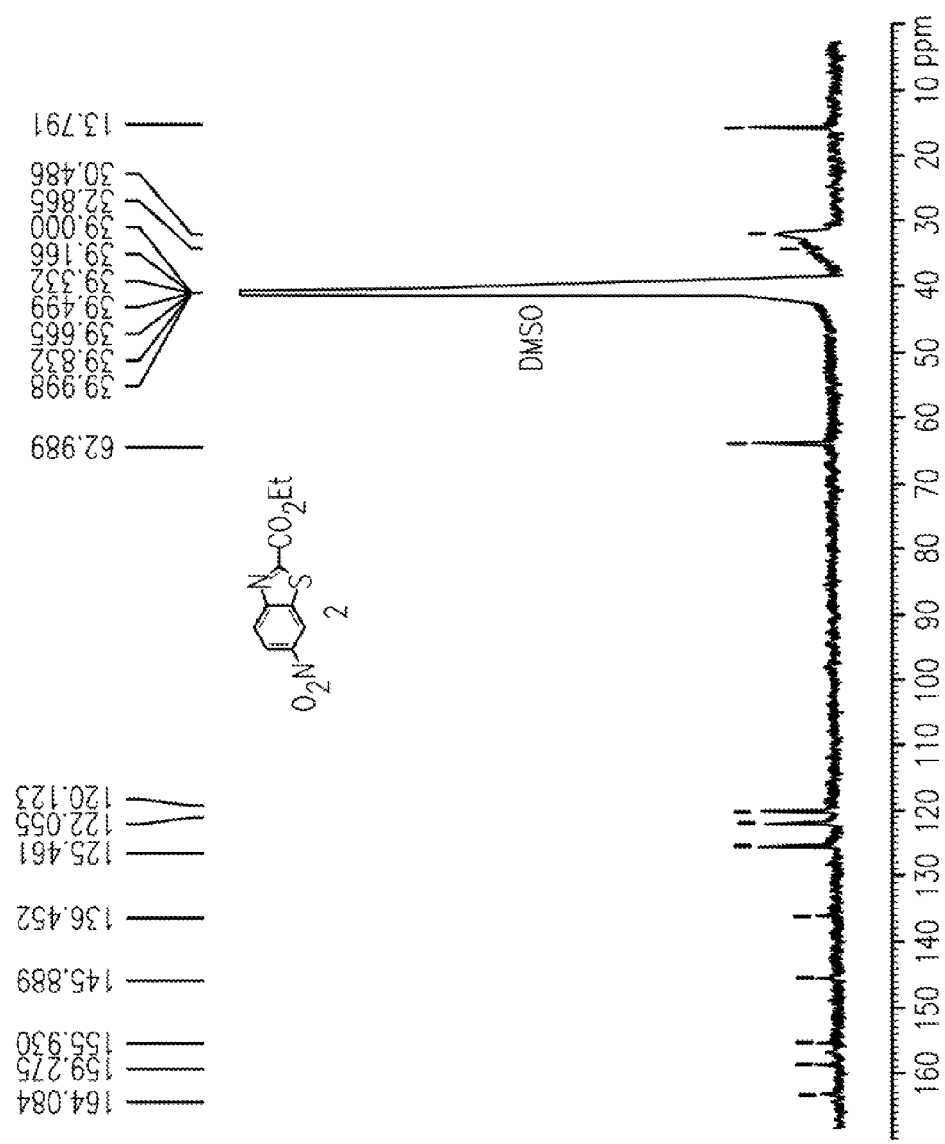
FIG. 4B shows nuclear magnetic resonance ($^{13}$C-NMR) spectra of ethyl 6-nitrobenzothiazole-2-carboxylate 2 obtained on a Bruker 500 MHz machine in $d_6$-DMSO.
Figure 4C:
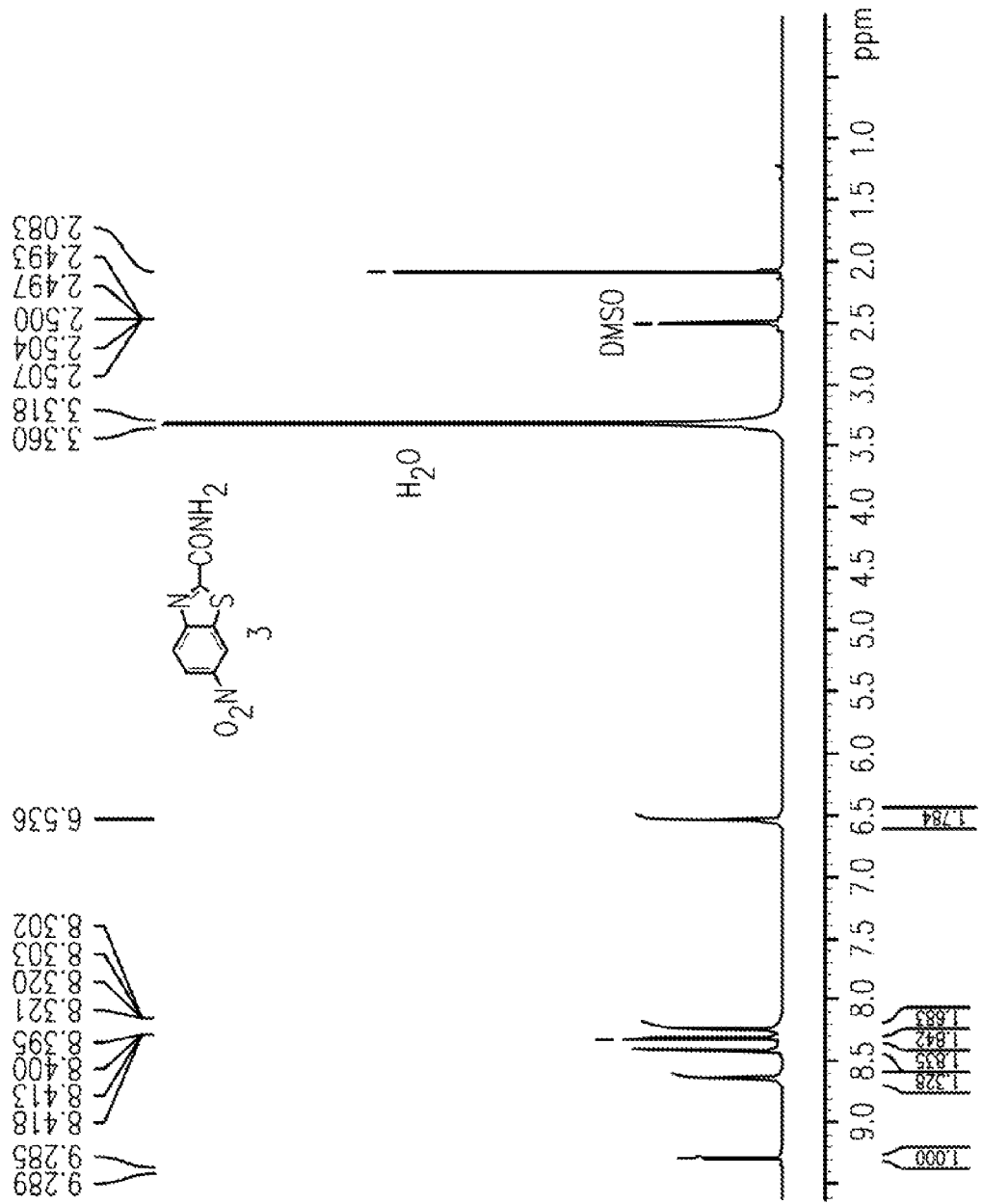
FIG. 4C shows a nuclear magnetic resonance ($^1$H-NMR) spectra of 6-nitrobenzothiazole-2-carboxamide 3 obtained on a Bruker 500 MHz machine in $d_6$-DMSO.
Figure 4D:
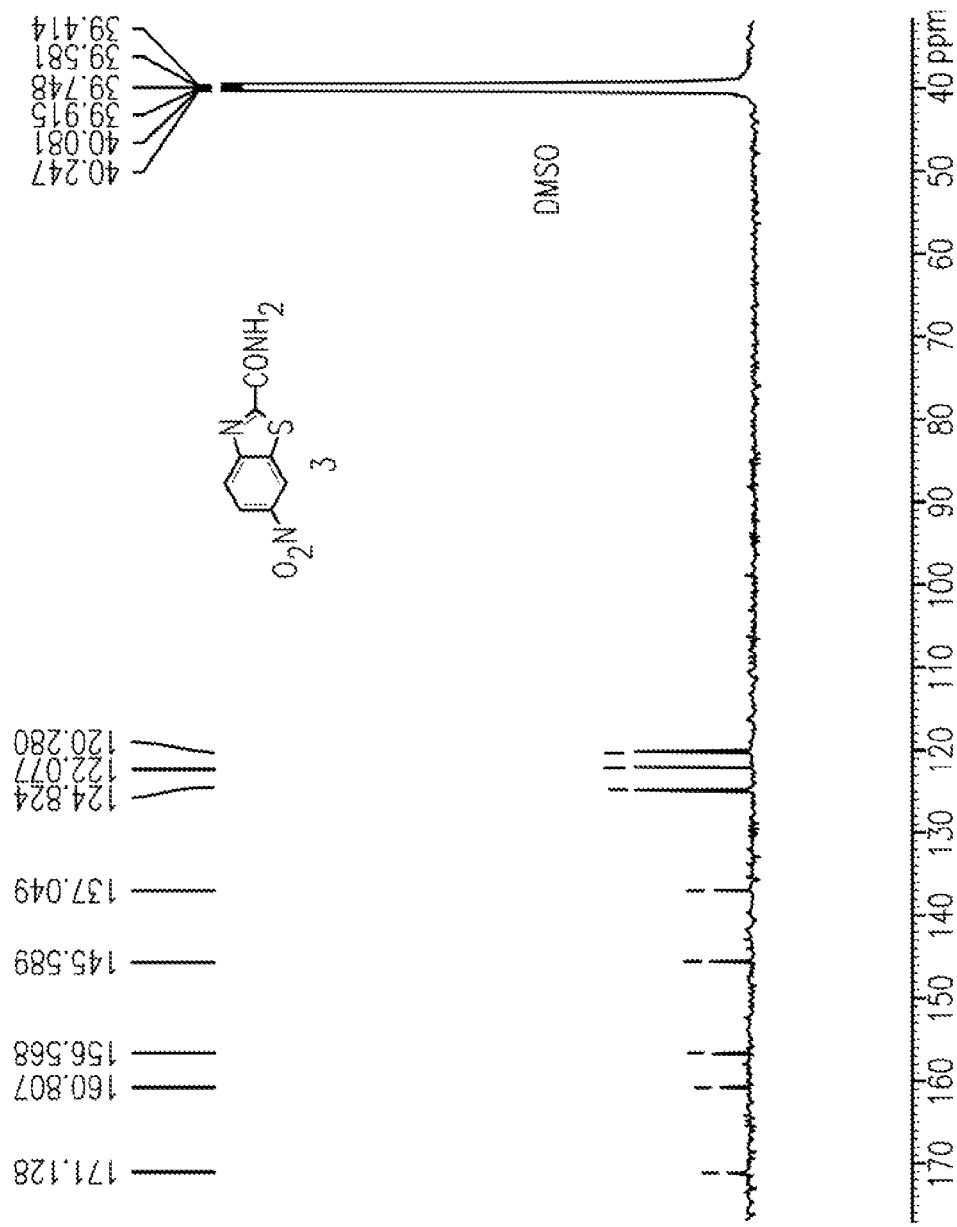
FIG. 4D shows Nuclear magnetic resonance ($^{13}$C-NMR) spectra of 6-nitrobenzothiazole-2-carboxamide 3 obtained on a Bruker 500 MHz machine in $d_6$-DMSO.
Figure 4E:
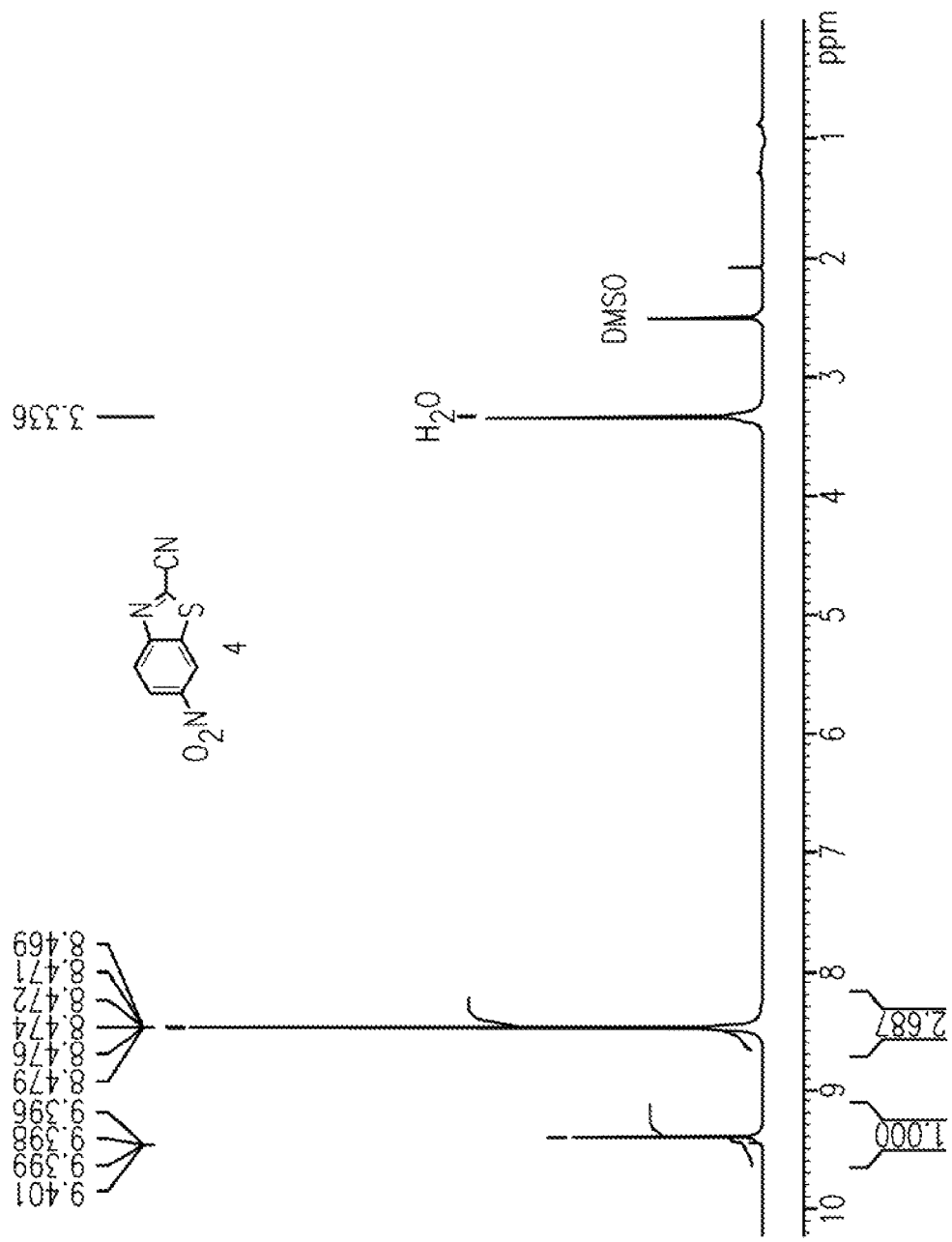
FIG. 4E shows a nuclear magnetic resonance ($^1$H-NMR) spectra of 2-cyano-6-nitrobenzothiazole 4 obtained on a Bruker 500 MHz machine in $d_6$-DMSO.
Figure 4F:
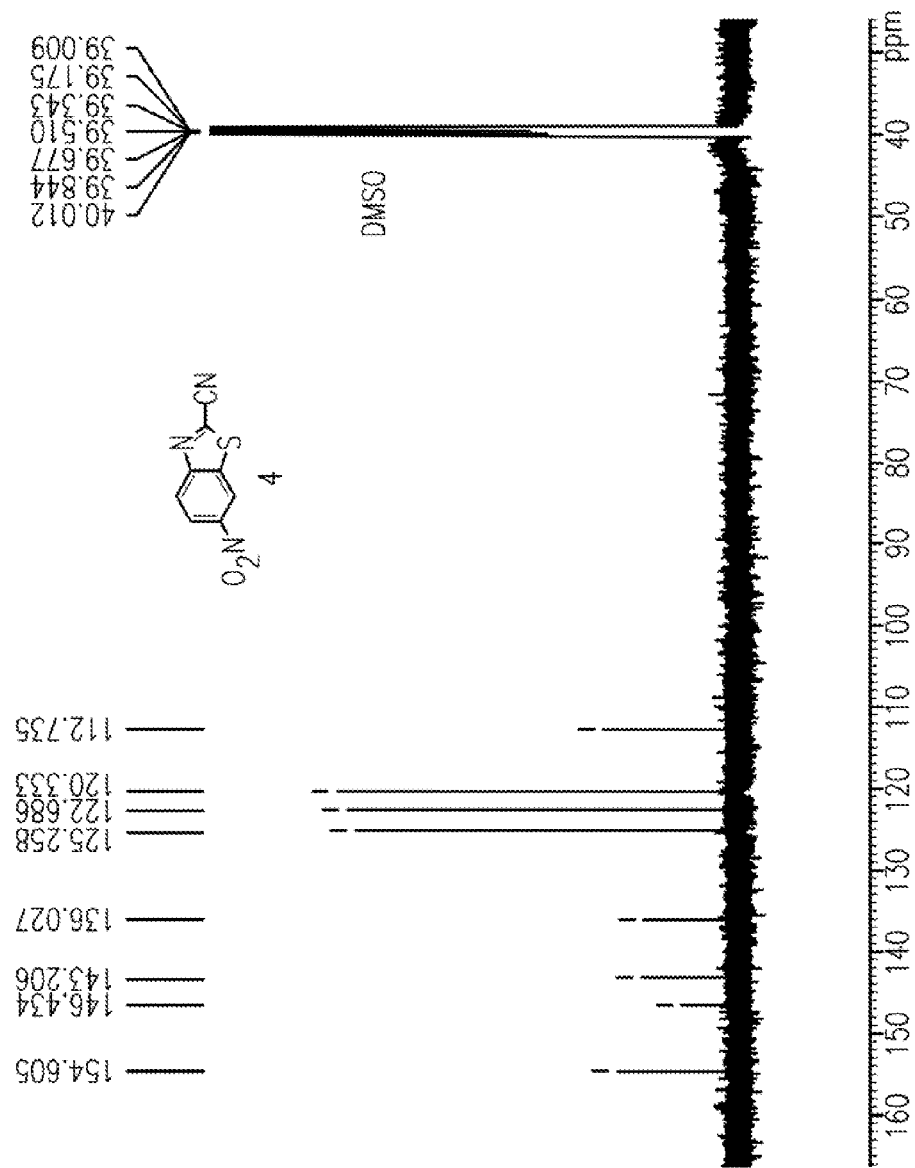
FIG. 4F shows a nuclear magnetic resonance ($^{13}$C-NMR) spectra of 2-cyano-6-nitrobenzothiazole 4 obtained on a Bruker 500 MHz machine in $d_6$-DMSO.
Figure 4G:
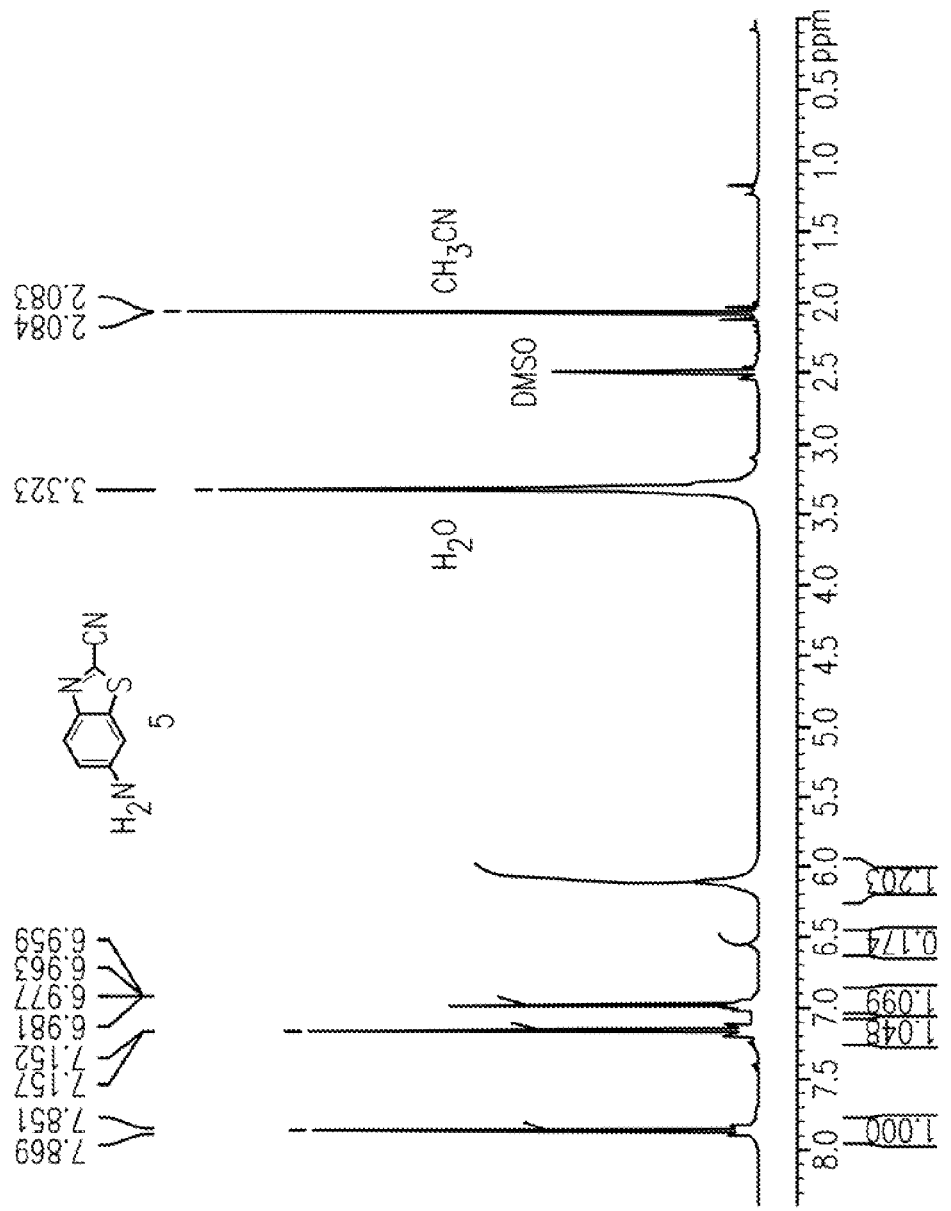
FIG. 4G shows a nuclear magnetic resonance ($^1$H-NMR) spectra of 2-cyano-6-aminobenzothiazole 5 obtained on a Bruker 500 MHz machine in $d_6$-DMSO.
Figure 4H:
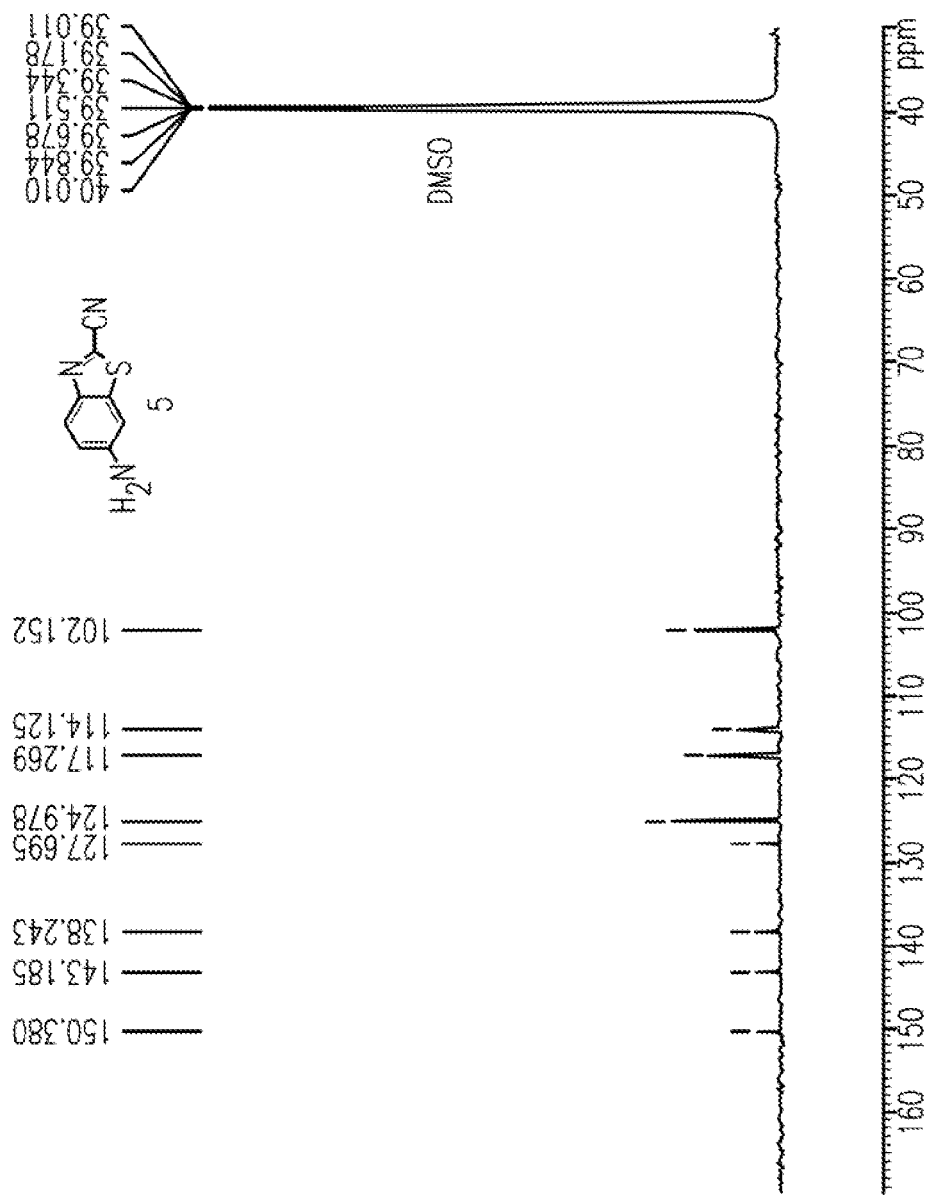
FIG. 4H shows a nuclear magnetic resonance ($^{13}$C-NMR) spectra of 2-cyano-6-aminobenzothiazole 5 obtained on a Bruker 500 MHz machine in $d_6$-DMSO.
Figure 4I:
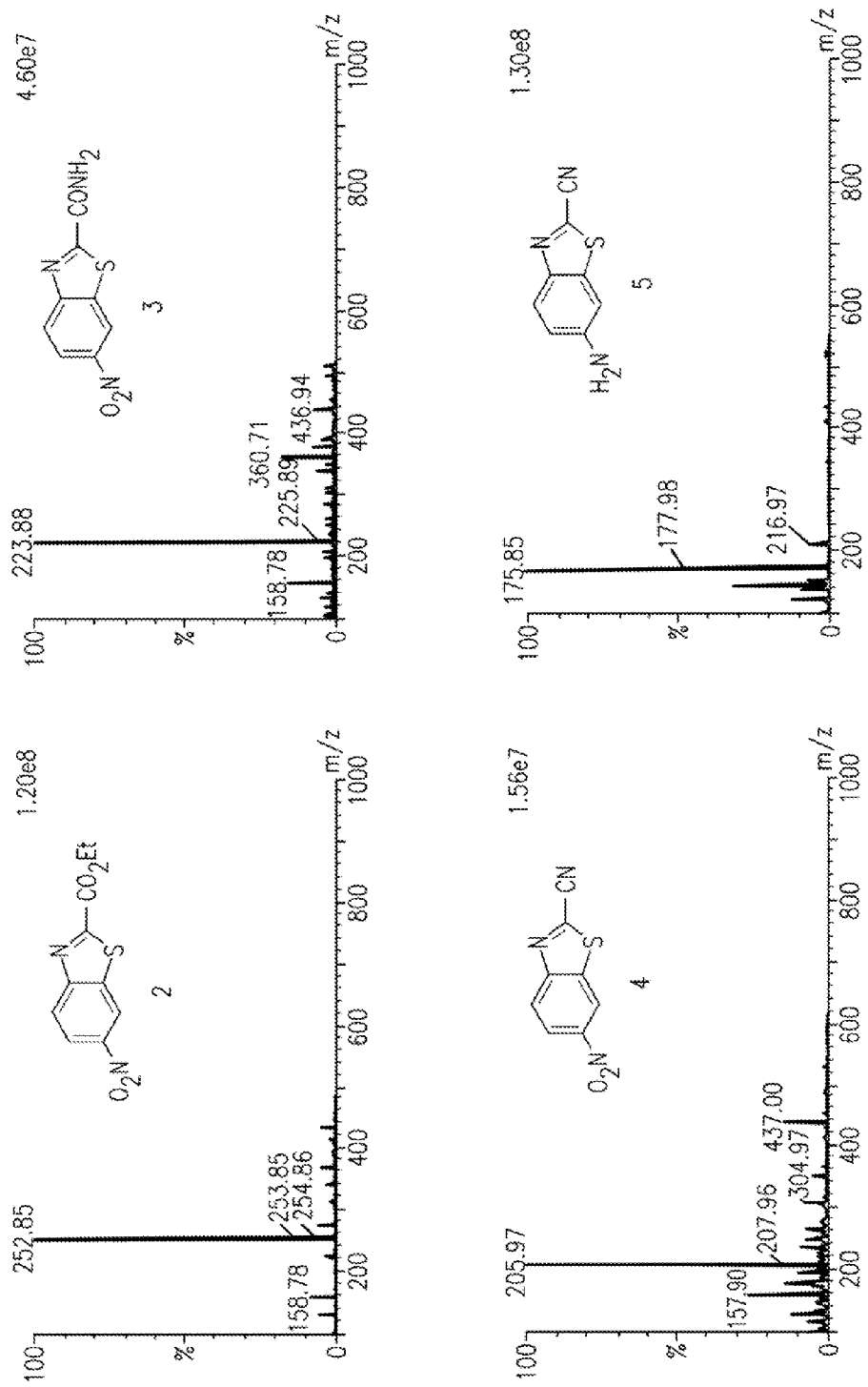
FIG. 4I shows Mass spectra were acquired on a Micromass Quattro Micro API mass spectrometer operating in positive ion mode. The samples were dissolved in MeCN/H$_2$O (1:1), 0.1% formic acid for mass spectrometry analysis.

In an embodiment, wherein $X_1$ is O the method can be performed as schematically illustrated in FIG. 3. In particular a free radical method can be used to generate 2-carboxyethylester-6-nitrobenzothiazole from commercially available 6-nitrobenzothiazole according to procedures exemplified in Example 1.

In the exemplary illustration of FIG. 3, the process further comprises converting the 2-carboxyethylester-6-nitrobenzothiazole into a carboxamide which in some embodiments can be carried out using suitable reagents to introduce nitrogen in the functional group of formula (II) which are identifiable by a skilled person upon reading of the present disclosure. Exemplary procedures using reagents such as potassium amide or tritylamine and use a diverse range of catalysts such as various forms of palladium. In an exemplary procedure, nitrogen is introduced by adding ammonia gas in methanol with 100% conversion (TLC and analytical HPLC) (see Example 2.

In the exemplary illustration of FIG. 3, the 6-nitrobenzothiazole-2-carboxamide is then converted into a 2-cyano-6-nitrobenzothiazole. In some embodiments, this conversion can be performed by dehydration of the carboxamide to a nitrile which can be carried out for example using $POCl_3$ in pyridine, again in quantitative yield (TLC and analytical HPLC). The corresponding nitrile can then be purified using gravity column silica chromatography before the final step and starting material 6-nitrobenzothiazole can be recovered (see Example 3). Additional procedures to perform dehydration comprise procedures which use silanes, zirconium catalysts, palladium catalysts, phosphines according to techniques identifiable by a skilled person. Additional procedures and techniques which are also suitable for the conversion of carboxamide to a nitrile are also identifiable by a skilled person.

In the exemplary illustration of FIG. 3, the reduction of the NO2 group in C6 to a NH2 is performed following conversion of the C2 into a nitrile group as a final reaction to generate the 6-amino-6-deoxy-D-luciferin, D-aminoluciferin, precursor. The reduction of NO2 in C6 can be performed using methods identifiable by a skilled person, such as, procedures performed using stannous chloride in ethanol exemplified in the Example section. In those reactions, a sufficient number of equivalents of the reductant (e.g. about 2.5 to about 5 eq) can be used to reduce the nitro group in a predetermined amount of time (e.g. about 2 h). Silica chromatography purification can also be used to yield D-aminoluciferin precursor with high purity for subsequent coupling reactions (e.g. to amino acids and peptides) (see Example 4).

In some embodiments according to the illustration of FIG. 3, reactions are selected so that subsequent conversions of ethyl 6-nitrobenzothiazole-2-carboxylate are not impeded by a mixture of ethyl 6-nitrobenzothiazole-2-carboxylate and 6-nitrobenzothiazole, and therefore, the mixture can be carried forward without purification. In some of those embodiments, the synthesis is particularly suitable for actual production of material for use in assays, kits, and additional applications identifiable by a skilled person since purification is not necessary.

A skilled person will be able to identify variants of the procedure schematically illustrated in FIG. 3 with other functional groups of formula (I) and (II) and with reduction of the $NO_2$ in C6 position at different stages before the conversion of the functional group in C2 upon reading of the present disclosure as also exemplified by the Examples section and figures.

Figure 5:
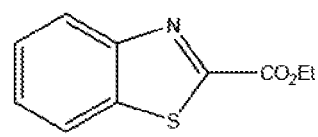
FIG. 5 shows schematic representation of a method to provide 2-cyano-6-aminobenzothiazole from a monofunctional benzothiazole according to an embodiment herein described. In particular, the illustration of FIG. 5 shows a general scheme for syntheses of 2-cyano-6-aminobenzothiazole, starting with a ethyl benzothiazole-2-carboxylate according to an embodiment herein described.
Figure 5:
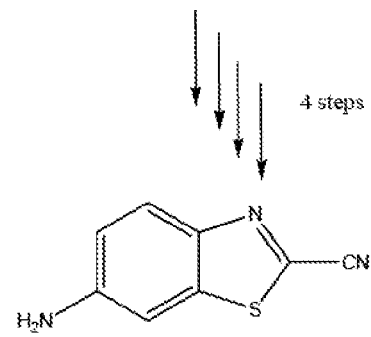

For example additional exemplary reaction schemes starting from a different monofunctional benzothiazole herein described, are schematically illustrated in FIG. 5 which shows a specific functional group of formula (II) wherein $X_1$ and $X_2$ are oxygen and R is an ethyl group. In the exemplary illustration of FIG. 5, the starting monofunctional benzothiazole is ethyl benzothiazole-2-carboxylate and the nitration of C6, and conversion of the ethyl ester C2 group into a carboxamide and then to a nitrile group can be performed according to any of the procedure herein described.

Figure 6A:
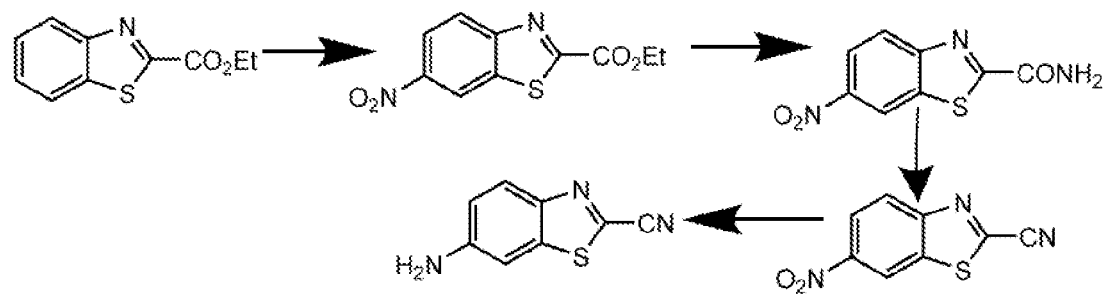
FIG. 6 shows a schematic representation of the four steps depicted in FIG. 5 according to an embodiment herein described. In particular, in the illustration of FIG. 6A, the ethyl benzothiazole-2-carboxylate is first nitrated to provide a ethyl 6-nitrobenzothiazole-2-carboxylate; the ester group in position C2 of the resulting ethyl 6-nitrobenzothiazole-2-carboxylate is then expected to be reduced to a carboxamide group and then to a cyano group. In the illustration of FIG. 6B nitration of C6 of the benzothiazole is performed after the reducing the carboxylate group in C2 to a carboxamide and before the expected conversion of the carboxamide group to a cyano group. In the illustration of FIG. 6C nitration of C6 of the benzothiazole is performed after reducing the carboxylate group in C2 to a carboxamide and before the expected conversion of the carboxamide to a cyano group, followed by a reduction of the C6 position to an amino group.
Figure 6B:
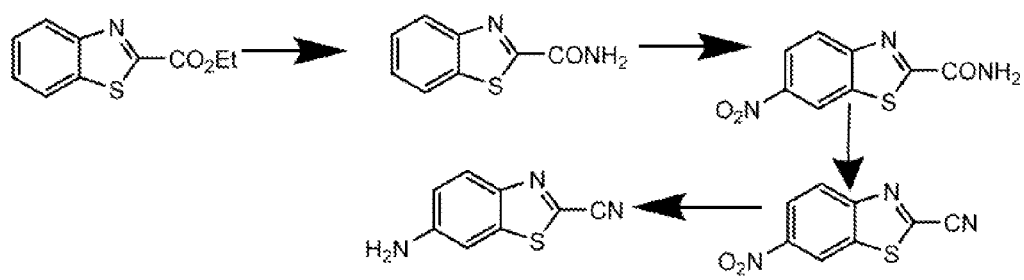
Figure 6C:
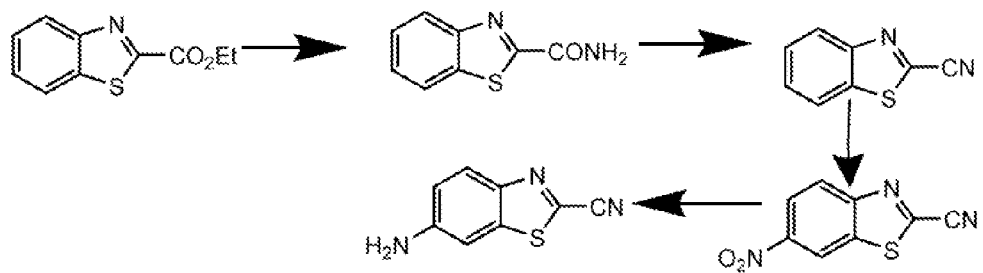
Figure 7:
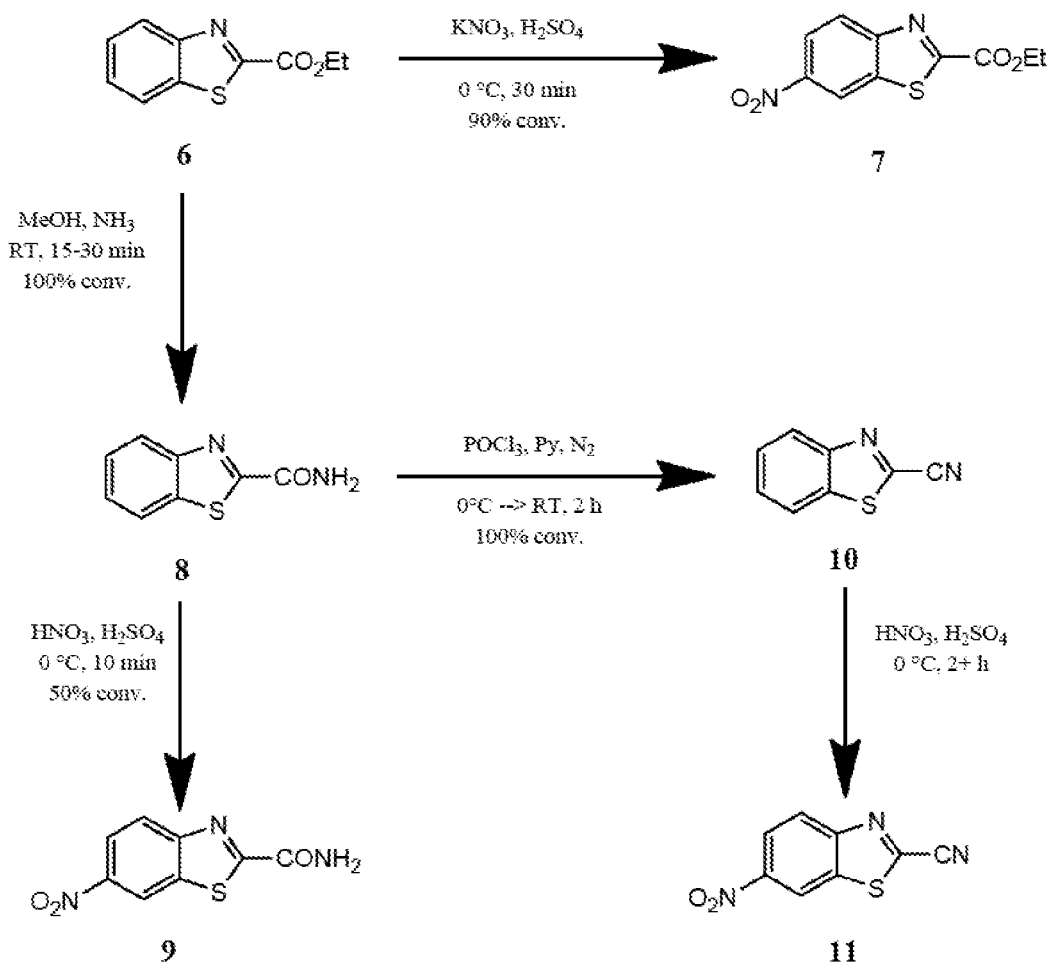
FIG. 7 shows schematic representation of a method to provide 2-cyano-6-aminobenzothiazole from a monofunctional benzothiazole according to an embodiment herein described. In particular, the illustration of FIG. 7 shows synthetic routes consisting of a series of nitration reactions expected to generate the intermediate derivatives to the D-aminoluciferin precursor, 2-cyano-6-aminobenzothiazole according to embodiments herein described.
Figure 8:
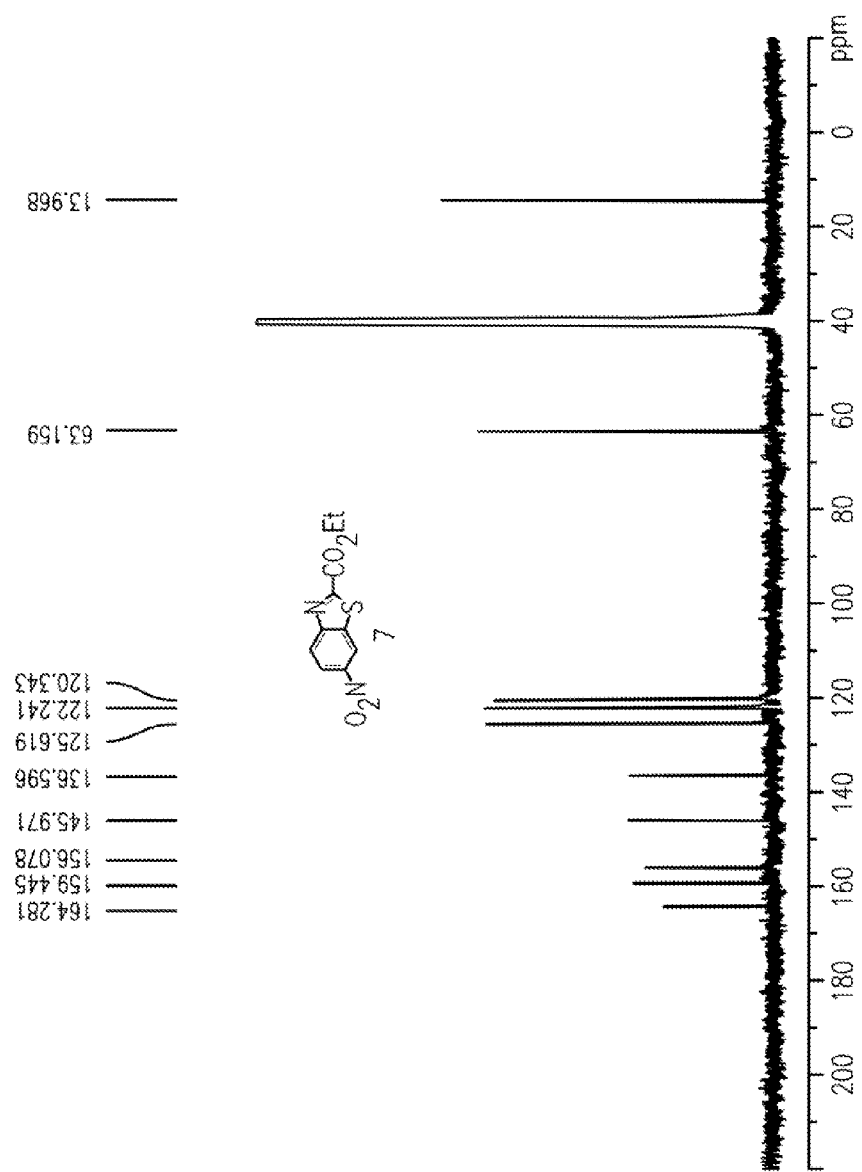
FIG. 8 shows a nuclear magnetic resonance spectra for a compound herein described. In particular

Some specific routes are further illustrated in FIGS. 6 and 7. In particular, FIGS. 6 and 7, show specific schemes for alternative synthesis of 2-cyano-6-aminobenzothiazole starting with a commercially available 2-carboxyethyl ester. As shown in the exemplary illustration of FIG. 6, it is expected that nitration can be performed at any point and the possibility to nitrate either the ester (FIG. 6A) or the carboxamide (FIG. 6B) has been demonstrated.

In the exemplary illustration of FIG. 6A, the monofunctional benzothiazole is ethyl benzothiazole-2-carboxylate and the 2-cyano-6-aminobenzothiazole can be provided following nitration and subsequent reduction of the benzothiazole. Nitration of the commercially available, ethyl benzothiazole-2-carboxylate was also carried out using concentrated $H_2SO_4$ and $KNO_3$ resulting in a mixture of 2-carboxyethylester-6-nitrobenzothiazole with starting material (TLC). Gravity silica column chromatography of 2-carboxyethylester-6-nitrobenzothiazole proved challenging to separate from starting material 2-carboxytheylester-benzothiazole (10% yield). (see Example 5).

In the exemplary illustration of FIGS. 6B and 6C, converting the ethyl benzothiazole-2-carboxylate into a 2-carboxamide-benzothiazole is carried out with ammonia (e.g. using ammonia gas in methanol with 100% conversion (TLC, analytical HPLC) see Example 6). Without purification 2-carboxamide-benzothiazole can be reacted (e.g. with conc. $H_2SO_4$ and $HNO_3$) to yield a mixture of 6-nitrobenzothiazole-2-carboxamide and 2-carboxamide-nitrobenzothiazole (~50% by TLC) (see Example 7). Suitable techniques can be used to separate the mixture (for example gravity silica column chromatography of 6-nitrobenzothiazole-2-carboxamide (~38% yield) see Example 7).

In some embodiments, converting the 2-carboxamide-benzothiazole to a corresponding nitrile in C2 position can be performed elimination reactions and additional reactions identifiable by a skilled person. In the methods herein described for example conversion of the C2 carboxamide can be performed by dehydration to the nitrile using suitable reagents such as phosphoryl chloride in pyridine, proceeding with quantitative conversion. In some of those embodiments, benzothiazole-2-carboxamide can be converted to the nitrile to yield 2-cyano-benzothiazole with 100% conversion (analytical HPLC, mass spect) (see Example 8). Without purification, the nitrile was reacted with $H_2SO_4/HNO_3$ and the reaction was monitored over time (over a period of ~2 h) via analytical HPLC. (see Example 11).

A skilled person will be able to identify alternative reactions schemes according to the illustration of FIGS. 5 to 7, wherein in the functional group (II) of the monofunctional benzothiazoles, $X_1$ and/or $X_2$ are S and/or R is provided by a different alkyl group (in particular a lower alkyl group) or a halogen (e.g. Cl), upon reading of the present disclosure. In any of those embodiments wherein the monofunctional benzothiazole used in methods and systems herein described does not initially comprise a nitro or amino group in position C6, the amino group is introduced at various stages as will be understood by a skilled person. For example in some embodiment, it is expected that the $NO_2$ group can be introduced using concentrated nitric and sulfuric acids, giving regioselectivity for the C6 position over the C4,C5, or C7 positions of the benzothiazole ring presenting a carboxamide, before converting the carboxamide to a cyanide group. In some embodiments, the NH2 group can be introduced at any stage with other reactions which do not require nitration of the C6 position that will be identifiable by a skilled person upon reading of the present disclosure.

In an embodiment of methods and systems provide the D-aminoluciferin precursor the monofunctional benzothiazole is 6-nitrobenzothiazole. In some of those embodiments cyanation of the 2-position of 6-nitrobenzothiazole can be performed by forming a lithium salt of benzothiazole with butyllithium then reacting this with a soluble cyanide followed by quenching of excess butyl lithium with water[15]. Starting material and only a small amount of 6-nitrobenzothiazole-2-carbonitrile resulted. Direct cyanation of the C2 position of other monofunctional benzothiazoles herein described can be performed according to techniques and procedures identifiable by a skilled person upon reading of the present disclosure.

In some embodiments, the 6-amino-6-deoxy-D-luciferin, D-aminoluciferin, precursor obtained with any of the methods and/or systems herein described or provided using other methods can be coupled to an amino acid or peptide labeled to provide an amino acid-conjugated or a peptide conjugated-2-cyano-6-aminobenzothiazole.

As used herein the term "amino acid", "amino acid monomer", or "amino acid residue" refers to any of the twenty naturally occurring amino acids including synthetic amino acids with unnatural side chains and including both D and L optical isomers. The term "polypeptide" or "peptide" as used herein indicates an organic polymer composed of two or more amino acid monomers and/or analogs thereof. The term "polypeptide" includes amino acid polymers of any length including full length proteins and peptides, as well as analogs and fragments thereof. A polypeptide of three or more amino acids is also called a protein oligomer or oligopeptide. The term "amino acid analog" refers to an amino acid in which one or more individual atoms have been replaced, either with a different atom, isotope, or with a different functional group but is otherwise identical to its natural amino acid analog.

The term "couple" or "conjugate" as used herein indicates formation of a covalent bond between two compounds. Typically, in some embodiments, coupling or conjugation of the amino acid or to the amino group in 2-cyano-6-aminobenzothiazole can be performed with an efficient peptide coupling method such as DCC, or N-methyl morpholine and isobutylchloroformate, since the aniline amino group is relatively unreactive. In other embodiments, coupling or conjugation can be performed reactions suitable to form a urea/thiourea (NH(C=X)NH) or a carbamate/thiocarbamate (X(C=X)NH) linkage, where X=O or S.

The term "carbamate" as used herein indicates organic compounds derived from carbamic acid (NH2COOH). Specifically, the term refers to any salt or ester of carbamic acid with the general structure R8O—CO—NR9R10, where R8, R9, and R10 are same or different and are organic substituents with one or two possibly formed by H. The term "thiocarbamate" as used herein indicates sulfur analogues of carbamates, where one of the oxygen atoms (O) in a carbamate is replaced by a sulfur atom (S). Specifically, there are two structurally isomeric types of thiocarbamates: O-thiocarbamates, ROC(=S)NR2, where the carbonyl group (C=O) is replaced with a thiocarbonyl group (C=S) and S-thiocarbamates, RSC(=O)NR2, where the R—O— group is replaced with an R—S— group. Further, O— and S— thiocarbamates can interconvert, for example in the Newman-Kwart rearrangement.

Figure 9:
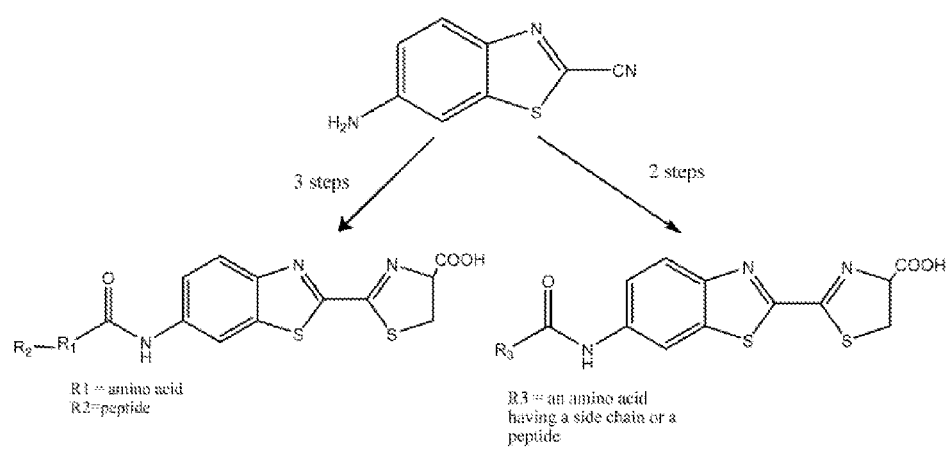
FIG. 9 shows a schematic representation of a method to provide an amino acid or a peptide labeled with 6-amino-6-deoxy-D-luciferin according to an embodiment herein described. In particular, the illustration of FIG. 9, schematically shows a 3-step process of the synthesis of 2-cyano-6-aminobenzothiazole, the precursor to 6-amino-6-deoxy-D-luciferin, conjugated to single amino acids (R1=one of the 20 amino acids) followed by subsequent conjugation to $R_2$ ($R_2$=either another amino acid or a peptide sequence) and then cyclization of the ring structure to generate bioluminescent probes according to embodiments herein described.
Figure 10A:
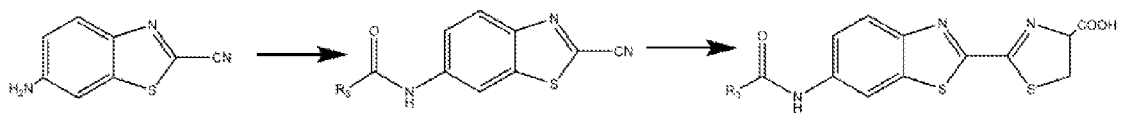
FIG. 10A shows a schematic representation of a conjugation of single amino acids to 2-cyano-6-aminobenzothiazole, the precursor to 6-amino-6-deoxy-D-luciferin (D-aminoluciferin) and subsequent schematic representation of a cyclization of ring structure to form amino acid conjugated 6-amino-D-luciferin.
Figure 10B:
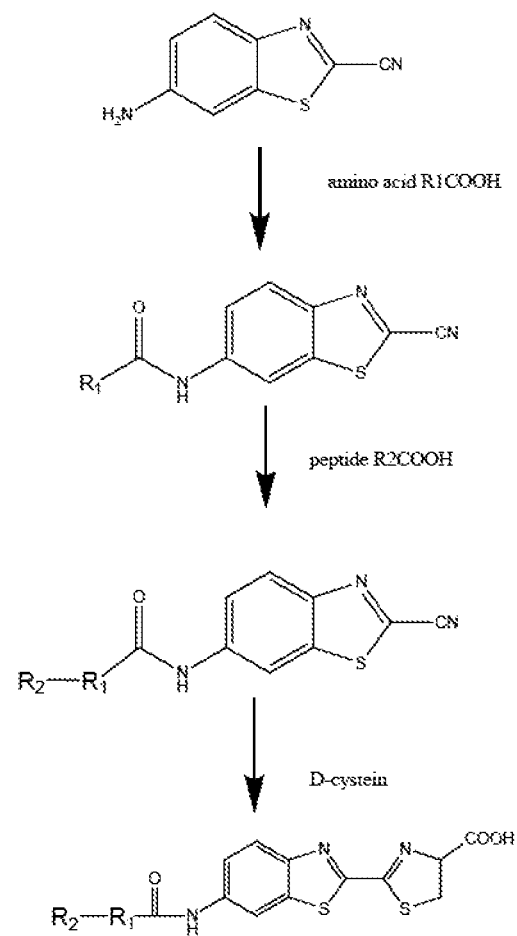
FIG. 10B shows a schematic representation of a method to provide an amino acid or a peptide labeled with 6-amino-6-deoxy-D-luciferin from a 2-cyano-6-aminobenzothiazole according to an embodiment herein described. In particular, the schematics of FIG. 10B show a generalization of a step-wise process for preparation of the precursor to D-aminoluciferin comprising first conjugating a single amino acid (R1), followed by subsequent conjugation with a longer peptide sequence (R2), and then formation of the peptide-conjugated D-aminoluciferin substrate via cyclization.
Figure 11:
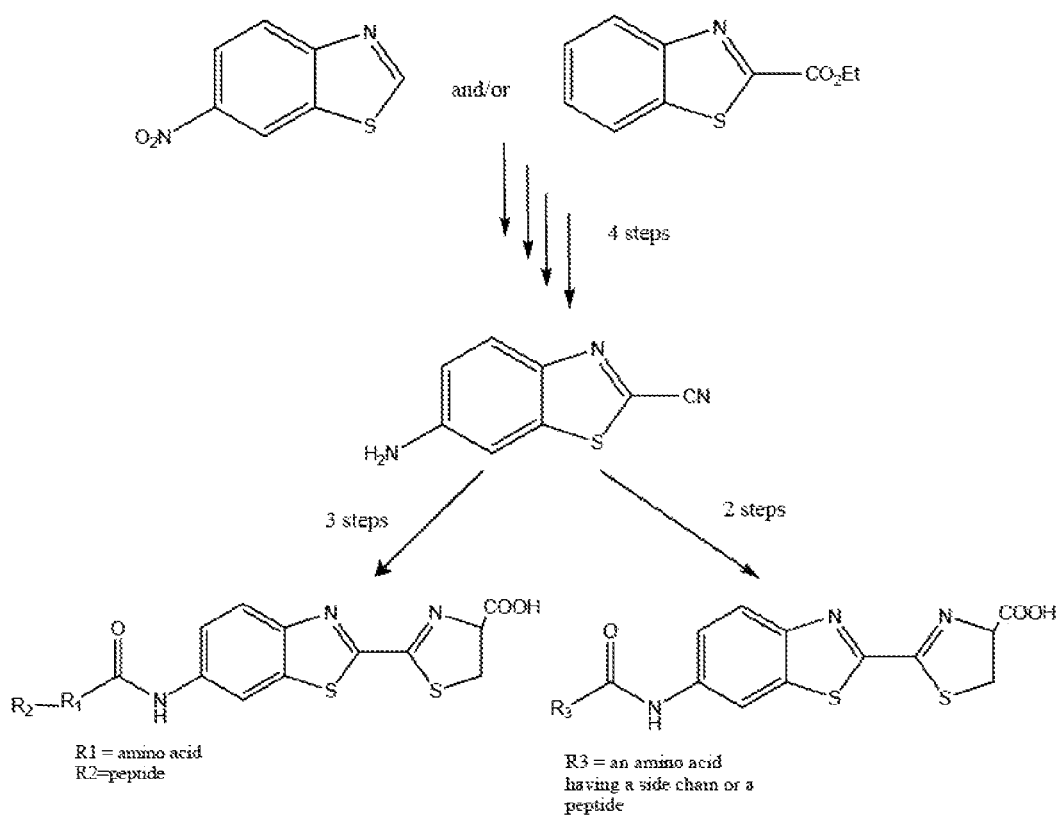
FIG. 11 shows a schematic representation of a method to provide an amino acid or a peptide labeled with 6-amino-6-deoxy-D-luciferin from a monofunctionalized benzothiazole according to an embodiment herein described
Figure 12:
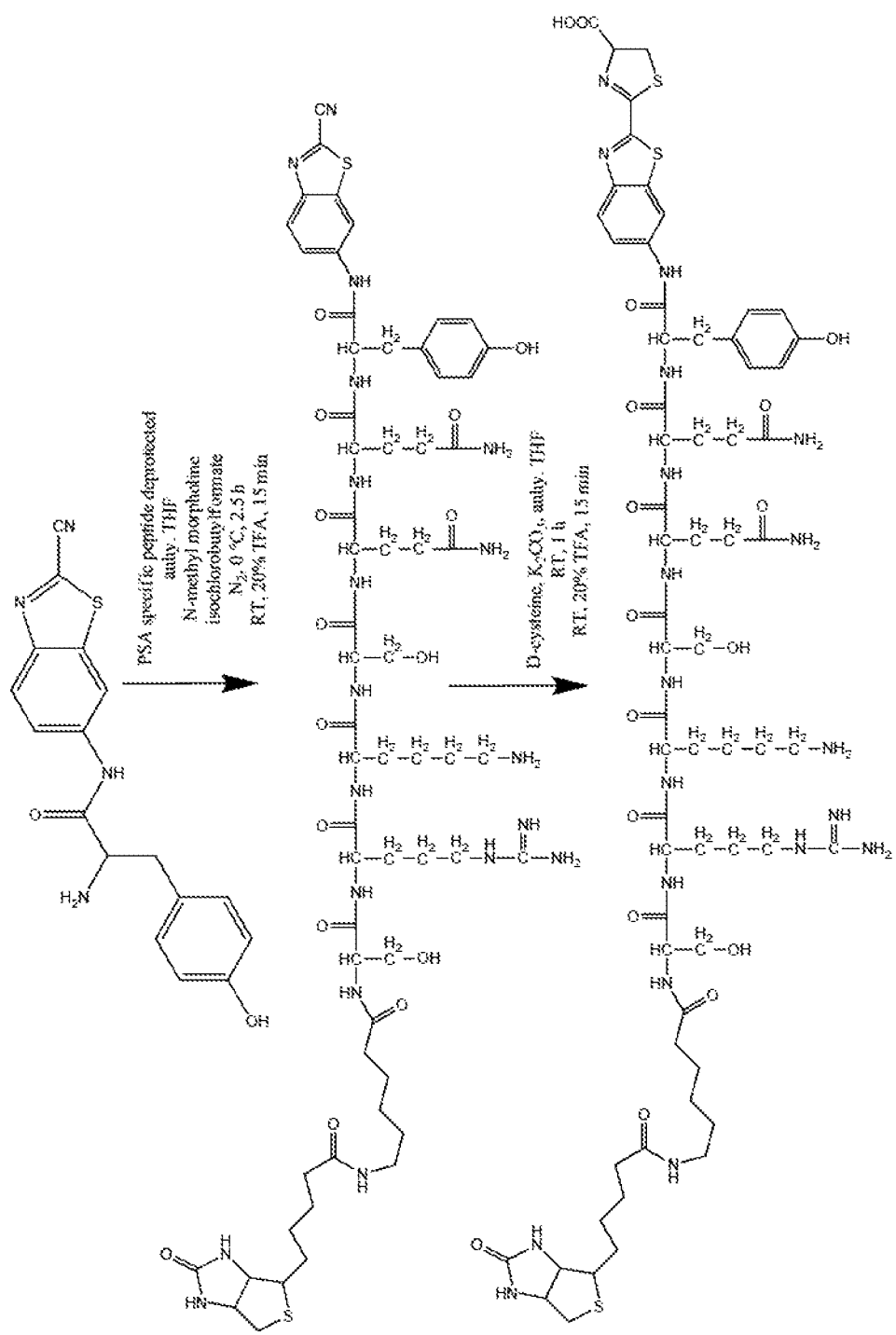
FIG. 12 shows a schematic representation of a method to provide an amino acid or a peptide labeled with 6-amino-6-deoxy-D-luciferin from a 2-cyano-6-aminobenzothiazole according to an embodiment herein described. In particular, the schematics of FIG. 13 show a specific example of the method schematically illustrated in FIG. 11 where $R_1$ is a tyrosine amino acid and $R_2$ is a specifically designed biotin-labeled peptide sequence that can be recognized by the serine protease, prostate specific antigen. The biotin functional group on the end of the peptide sequence facilitates coupling to a streptavidin compound wherein this final compound could be utilized in an assay system.
Figure 13:
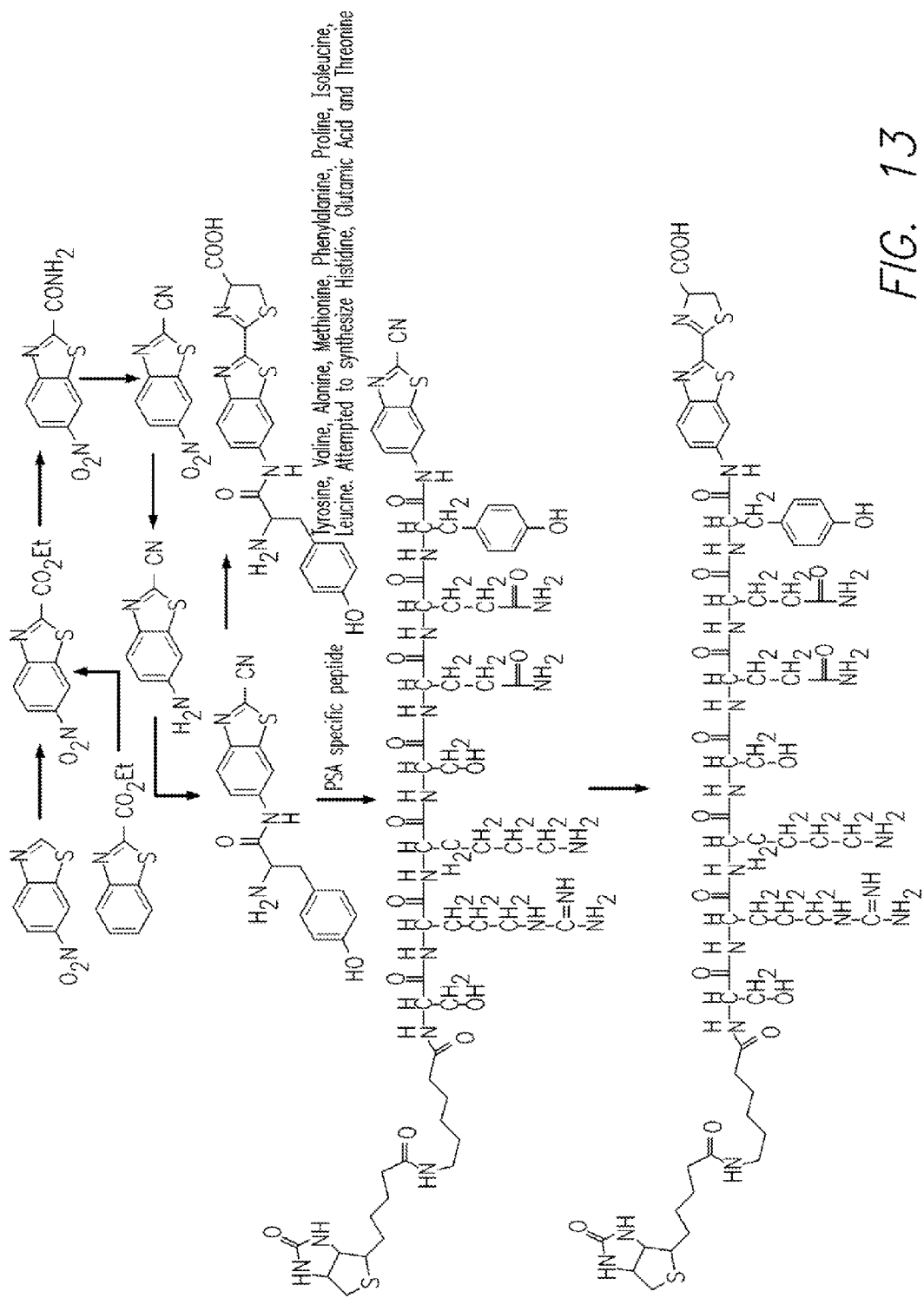
FIG. 13 shows a schematic representation of a method to provide an amino acid or a peptide labeled with 6-amino-6-deoxy-D-luciferin from a monofunctionalized benzothiazole according to an embodiment herein described.

In particular, in some embodiments coupling of the peptide with the precursor can be performed according to a two step process schematically illustrated in FIGS. 9 and 10 wherein a process is illustrated that comprises conjugating an amino acid and/or a peptide to the precursor. In particular, in some embodiments the conjugation between amino acid and/or peptide can be performed in a two step reaction wherein the amino acid or peptide is first conjugated with the peptide and then the resulting amino acid-conjugated or peptide-conjugated precursor is reacted with cysteine to provide an amino acid-conjugated D-aminoluciferin or a peptide-conjugated D-aminoluciferin (FIG. 10A). In other embodiments, a three step reaction is performed wherein the an amino acid-conjugation with the precursor is performed, followed by conjugation with the specific peptide sequence, and then reacting with D-cysteine to provide the peptide-conjugated D-aminoluciferin (FIG. 10B)

In some embodiments, conjugation of the amino group of the 2-cyano-6-aminobenzothiazole to single amino acids or peptides can be achieved using isobutylchloroformate activation of the free acid of the amino acid in the presence of N-methyl morpholine in THF as previously reported.[11,13] (see Example 10). In some embodiments, conjugation of the amino group of the 2-cyano-6-aminobenzothiazole to single amino acids can be achieved using carbodiimide activation. In particular carbodiimide activation involves attack of the carboxylate oxygen on the central carbodiimide carbon, creating a leaving group with that oxygen atom according to reactions identifiable by a skilled person. The amine then attacks the carboxyl carbonyl, displacing the now urea leaving group. The insolubility of some ureas can in some cases help drive the reaction.

In some embodiments, suitable amino acids to be conjugated with the D-aminoluciferin precursor comprise the 20 naturally occurring amino acid amino acids, including Isoleucine, Alanine, Leucine, Asparagine, Lysine, Aspartic Acid, Methionine, Cysteine, Phenylalanine, Glutamic Acid, Threonine, Glutamine, Tryptophan Glycine, Valine, Proline, Serine, Tyrosine, Arginine, Histidine, and additional amino acids such as Selenocysteine Ornithine, and Taurine. In particular, in some embodiments, the amino acids comprise in particular Alanine, Valine, Isoleucine, Leucine, Tyrosine, Methionine, Threonine. In some embodiments, suitable amino acids to be conjugated with the D-aminoluciferin precursor comprise in particular Phenylalanine, Histidine and Glutamic Acid. In some embodiments, amino acids comprising a side chain (hydrophobic, hydrophilic, acid or basic in nature) can be coupled with the precursor and then cyclized with D-cysteine to yield the amino acid-conjugated 6-amino-6-deoxy-D-luciferin, which it is expected to contribute to varying pharmacokinetics/pharmacodynamics behaviors as measured by bioluminescence.

In some embodiments, the amino acids comprise a side chain, which have been surprisingly found to be labelable with the precursor and then converted in to functional amino acid labeled with D-luciferin despite the expected modifications in biodistribution (pharmacokinetics/pharmacodynamics) as measured by bioluminescence In particular in some embodiments, the amino acid is an amino acid having a hydrophobic side chain (including for example Alanine, Isoleucine, Leucine, Methionine, Phenylalanine, Tryptophan, Tyrosine and Valine). In some embodiments, the amino acid is an amino acid having a non-polar uncharged side chain (including for example Serine, Threonine, Asparagine and Glutamine). In some embodiments, the amino acid is an amino acid having an electrically charged side chain (including for example Arginine, histidine and Lysine, Aspartic acid and Glutamic acid).

In some embodiments, an intermediate in the synthesis of peptide labeled at the carboxy terminus with 6-amino-6-deoxy-D-luciferin formed by a substituted 2-cyano-6-aminobenzothiazole can be provided.

In some embodiments, methods and systems to provide a peptide labeled at the carboxy terminus with 6-amino-6-deoxy-D-luciferin from a monofunctional benzothiazole. In some embodiments, the peptide can be of at least 6 or 7 amino acid resides in length and in some of those embodiments the system can comprise a further label such a biotin label or a linker possibly attached and in particular conjugated to the peptide at the terminus opposite to the terminus where the D-amino luciferin is conjugated directly or indirectly through conjugation to an amino acid-conjugated D-aminoluciferin precursor. Without any intention of being limiting and for guidance purpose only it is expected that use of the three step process schematically illustrated in FIG. 10B will be particularly useful for synthesis of a peptide with a sequence of 5 amino acid residues or longer and/or to a peptide further labeled with biotin or other labels. In particular, in some of those embodiments, the D-aminoluciferin precursor is then first reacted with an amino acid and then redirectly with a long peptide chain thus allowing conjugation when the amino group on the precursor is not reactive enough to directly conjugate the peptide chain in an efficient manner according to an experimental design.

In an embodiment, a method and system to provide a peptide labeled with 6-amino-6-deoxy-D-luciferin is described. The method comprises conjugating the peptide with an amino acid-conjugated 2-cyano-6-aminobenzothiazole to provide a peptide-conjugated 2-cyano-6-aminobenzothiazole, the conjugating performed to allow formation of a peptide bond between the amino group of the amino acid-conjugated 2-cyano-6-aminobenzothiazole and a carboxylic group of the peptide. The method further comprises reacting the peptide-conjugated 2-cyano-6-aminobenzothiazole with D-cysteine to provide a peptide-conjugated 6-amino-6-deoxy-D-luciferin. The system comprises one or more peptides, peptide-conjugated 6-amino-2-cyanobenzothiazole and/or amino acid-conjugated 2-cyano-6-aminobenzothiazole for simultaneous combined or sequential use in the method to provide a peptide labeled with 6-amino-6-deoxy-D-luciferin herein described.

In some embodiments, modification of D-luciferin, 6-hydroxy-D-luciferin, to D-aminoluciferin, 6-amino-6-deoxy-D-luciferin, is expected to result in substrates that generate novel bioluminescent properties and offers the opportunity to expand the range of bioluminescence-based assays. D-aminoluciferin, with an amino group in the C6-position of the benzothiazole ring, allows conjugation of the optical reporter substrate to single amino acids and/or peptide sequences to generate novel assay probes with the peptide sequences targeting proteases.

In some embodiments, methods and systems herein described provide an alternate route for the synthesis of the precursor 2-cyano-6-aminobenzothiazole to D-aminoluciferin has been identified and used to generate material for subsequent conjugation to amino acids and peptide sequences for thorough investigation of the utility of bioluminescent protease probes.

In some embodiments, methods and systems herein described provide convenient synthetic route to D-aminoluciferin derivatives of peptides. In particular in some embodiments aminoluciferin derivatives herein described can be used in conjunction with firefly luciferase to report on cellular events in vivo as well as in bioluminescent assays. In particular, in some embodiments, the synthetic route begins with a monofunctional benzothiazole (either 6-nitrobenzothiazole or ethyl benzothiazole-2-carboxylate, proceeds through 2-cyano-6-aminobenzothiazole, and results in an amino acid or peptide conjugated to 6-amino-6-deoxy-D-luciferin.

In some embodiments a carboxylate-modified Luciferin, amino acid or peptide probe, is described, that comprises a D-luciferin molecule conjugated with the amino-terminus of an amino acid or peptide at the carboxyl group of said D-luciferin. In some of those embodiments, the carboxyl-terminus of the amino acid residue or peptide is blocked with a blocking group, such as an amide.

The carboxylate-modified luciferin, amino acid or peptide probe can be provided using methods and systems based on reactions performed on a resin base. In particular the amino acid or peptide can be provided on a resin base (e.g. by synthesizing the peptide on the resin base). A D-luciferin molecule can then be conjugated at the amino terminus of the peptide or amino acid on the resin bases via formation of a peptide bond. The resulting conjugate can be cleaved from the resin to produce a produce free carboxylate-modified luciferin, amino acid/peptide probe that can then be optionally purified if desired. In some embodiments the resin base is a chlorotrityl chloride (CTC) resin. In some embodiments synthesizing the peptide can be performed using standard Fmoc amino acid synthesis. Purification can be performed with techniques identifiable by a skilled person, for examples purification can be using reverse phase high performance liquid chromatography. Following purification the carboxyl-terminus of the said synthesized probe can be blocked using a blocking agent such as an amide.

The carboxylate-modified Luciferin, amino acid or peptide probe can be used to perform various assays and procedure aimed at detection of targets and/or reactions. For example in some embodiments the carboxylate modified luciferin amino acid or peptide can be used in connection with luciferase for releasing the D-luciferin molecule in the assay.

In particular, in some embodiments, carboxylate-modified luciferin probes are provided, where D-luciferin is modified at the carboxylic acid with amino acids/peptides to inhibit the reaction with the luciferase enzyme. In some of those embodiments, upon carboxypeptidase digestion of the amino acids conjugated to the D-luciferin, the free bioluminescent substrate is released for subsequent reaction with the luciferase enzyme. Further, in some embodiment, if the carboxyl-terminus of a D-luciferin-peptide sequence is blocked as a carboxamide or other suitable blocking agent, only upon proteolytic action is a free carboxylic acid generated for carboxypeptidase to begin digestion to release the D-luciferin. Combined together, these concepts are used to generate carboxylate-modified luciferin, amino acid/peptide probes and assays using such probes or any derivative thereof to monitor the action of proteases such as endoproteases or exopeptidase of interest.

The term "derivative" as used herein with reference to a first compound (e.g., D-aminoluciferin), indicates a second compound that is structurally related to the first compound and is derivable from the first compound by a modification that introduces a feature that is not present in the first compound while retaining functional properties of the first compound. Accordingly, a derivative of D-aminoluciferin, usually differs from the original D-aminoluciferin by modification of the substituents of the D-aminoluciferin that might or might not be associated with an additional function not present in the original D-aminoluciferin. The additional function, and the properties associated with D-aminoluciferin can be verified with methods and systems such as the ones described in the Examples section in connection with exemplary processes and derivatives herein described.

In some embodiments, derivatives of D-aminoluciferin herein described can be used in connection with several assays directed to in vitro or in vivo detection of targets and/or reactions.

The term "detect" or "detection" as used herein indicates the determination of the existence, presence or fact of a target or signal in a limited portion of space, including but not limited to a sample, a reaction mixture, a molecular complex and a substrate including a platform and an array. In particular, D-aminoluciferin typically provides bioluminescence which is an optically detectable signal.

In some embodiments, the D-aminoluciferin derivatives herein described can be used in assays where bioluminescent detection has extremely high sensitivity because the low background interference is not affected by cellular auto-fluorescence and other fluorescent contaminants and does not require extreme operation conditions. An example is provided by protease assays based on bioluminescence in connection with in vitro and in vivo applications which are identifiable by a skilled person. Proteases can be specific or non-specific in their action and therefore, a wide range of protease substrates may be required to characterize protease proteomics in different complex backgrounds (e.g. in vivo or serum). A wide variety of proteases are present in all living organisms and in protease activity levels are often a part of the host response to infection or disease.[16] Therefore, monitoring protease activity in both in vitro and in vivo experiments is potentially an early warning system for a particular diseased state before clinical symptoms occur.

Exemplary suitable assays are provided by in vitro assays for certain protease developed with different reporting techniques. The most common techniques are the proteolytic release of p-nitro aniline for UV detection, the proteolytic release of fluorescence dyes for fluorescence detection and mass spectrometry detection of proteolytic cleavage products. However, there are various problems associated with the detection techniques currently available when developing an assay for detecting specific reactions in a complex background (e.g. in vivo—the low sensitivity of UV absorption, auto-fluorescence of cells or fluorescent interference from chemical and natural products, and the vacuum and other expensive and cumbersome parts required for mass detection).

In methods and systems herein described, any of the above compounds can be synthesized or added according to techniques identifiable by a skilled person.

As disclosed herein, the compounds herein described can be provided as a part of systems to detect targets according to any of the methods described herein. The systems can be provided in the form of kits of parts.

In a kit of parts, the monofunctionalized benzothiazoles, reducing agents, and other reagents to perform the methods can be comprised in the kit independently. One or more compounds and reagents can be included in one or more compositions alone or in mixtures identifiable by a skilled person. Each of the one or more of compounds and reagents can be in a composition together with a suitable vehicle.

Additional reagents can include salts (such as $Mg^{2+}$) and reagents (e.g. ATP) and/or molecules suitable to enhance or favor the reaction according to any embodiments herein described and/or molecules, standards and/or equipment to allow detection of pressure temperature and possibly other suitable conditions. For example luciferin/luciferase as control reagents can be comprised in a kit to serve as the "parent compounds" that will provide the baseline for comparison to the modified bioluminescence substrates.

In particular, the components of the kit can be provided, with suitable instructions and other necessary reagents, in order to perform the methods here described. The kit will normally contain the compositions in separate containers. Instructions, for example written or audio instructions, on paper or electronic support such as tapes or CD-ROMs, for carrying out the assay, will usually be included in the kit. The kit can also contain, depending on the particular method used, other packaged reagents and materials (i.e. wash buffers and the like).

Further advantages and characteristics of the present disclosure will become more apparent hereinafter from the following detailed disclosure by way of illustration only with reference to an experimental section.

EXAMPLES

The methods system herein described and related intermediates and derivatives are further illustrated in the following examples, which are provided by way of illustration and are not intended to be limiting.

In particular, the following examples illustrate exemplary synthesis and uses of 2-cyano-6-aminobenzothiazole starting from 6-nitrobenzothiazole, ethyl 6-nitrobenzothiazole-2-carboxylate, and other compounds performed according to the reaction schemes summarized in FIGS. 1-13. A person skilled in the art will appreciate the applicability of the features described in detail for 2-cyano-6-aminobenzothiazole for additional compounds (e.g. additional monofunctional benzothiazole) having same or different chemical characteristics according to the present disclosure, and to related derivatives. The following examples also illustrated exemplary synthesis and uses of a carboxylate modified luciferin amino acid probe for bioluminescent protease assay according to reactions schemes summarized in FIGS. 14 and 15. A skilled person will appreciate the applicability of the features described in detail for the specific phenylalanine probe shown in the examples to other probes according to the present disclosure.

The following experimental procedures and characterization data were used for all compounds and their precursors exemplified herein.

General. Commercially available reagents and solvents were used as received without further purification. Anhydrous pyridine and phosphoryl chloride were purchased from Aldrich. 6-nitrobenzothiazole was purchased from Alfa Aesar. Anhydrous ammonia was purchased from Mattheson Tri-Gas, ethyl pyruvate from Fluka, ferrous sulfate from Mallinckrodt Chemicals, sodium bicarbonate from EMD Biosciences, and tin(II) chloride from Sigma. The amino acid compounds were purchased from NovaBioChem and the biotin-conjugated peptides were specifically designed and purchased from Peptides International.

Characterization/Instrumentation. Analytical thin layer chromatography (TLC) was carried out using aluminum sheets coated with silica gel 60 $F_{254}$. Reaction conversions were followed by analytical HPLC at 1 mL/min on an Agilent 1100 machine (Waters Symmetry C18, 5 µm, 4.2×150 mm column, diode array detector) with a linear gradient from 95% $H_2O$ (0.1% TFA) to 80% MeCN (0.1% TFA) over 15 ml. For analytical characterization, small portions were purified by semi-preparative HPLC at 10 mL/min on a Waters preparative machine (Waters Symmetry prep C18, 7 µm, 19×300 mm column, photodiode array detection) with a linear gradient from 90-95% $H_2O$ (0.1% TFA) to 50-90% MeCN (0.1% TFA) for 30-35 min. Semi-preparative HPLC fractions were collected and lyophilized using Kinetics Flexi-Dry freeze-dryer. Nuclear magnetic resonance (NMR) spectra were obtained on a Bruker 500 MHz machine in $d_6$-DMSO. Splitting patterns are denoted s, singlet; d, doublet; dd, doublet of doublets; t, triplet; m, multiplet; br s, broad singlet. Mass spectra were acquired on a Micromass Quattro Micro API mass spectrometer operating in positive ion mode. The samples were dissolved in MeCN/$H_2O$ (1:1), 0.1% formic acid for mass spectrometry analysis.

Example 1

Synthesis of ethyl 6-nitrobenzothiazole-2-carboxylate (2)

Ethyl 6-nitrobenzothiazole-2-carboxylate was synthesized from 6-nitrobenzothiazole according to the following reaction scheme.

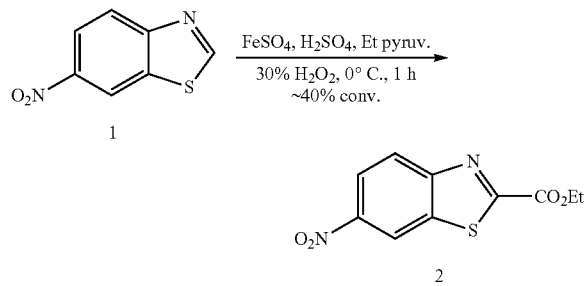

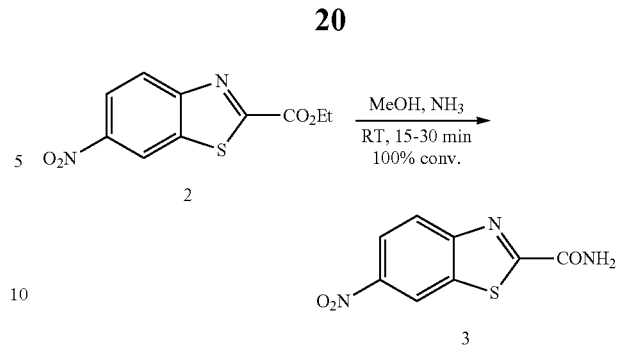

In particular, 6-nitrobenzothiazole 1 (16.7 mmol, 3.0 g) was suspended in 6.6 ml deionized $H_2O$. 2.7 ml conc. $H_2SO_4$ was added dropwise to the reaction flask. Separately, 30% $H_2O_2$ (167.6 mmol, 5.7 g) was added dropwise to a solution of ethyl pyruvate (75.6 mmol, 8.4 ml) at 0° C. The resultant oxyhydroperoxide solution and a solution of $FeSO_4 \cdot 7H_2O$ (48.9 mmol, 13.6 g) in 13.2 ml deionized $H_2O$ were simultaneously added dropwise to the 6-nitrobenzothiazole reaction flask at 0° C. After 30 min, the reaction was poured onto ice and basified with $NaHCO_3$ (pH from 2 to ~pH 6). The organic product 2 was washed with a saturated NaCl solution, extracted with EtOAc, dried over $Na_2SO_4$, and concentrated in vacuo. The material was additionally filtered with 200 proof EtOH yielding a pale yellow solid (~61% yield crude material). Agilent HPLC displayed partial conversion to the crude product at 10.4 min with a peak at 8.7 min corresponding to the starting material.

Compound 2 was used in the subsequent step without purification. For analytical characterization, a small portion was purified by semi-preparative HPLC at 10 mL/min on a Waters preparative machine (Waters Symmetry prep C18, 7 μm, 19×300 mm column, photodiode array detection) with a linear gradient from 95% $H_2O$ (0.1% TFA) to 90% MeCN (0.1% TFA) for 35 min yielding a large product peak at 27 min. The fractions were collected and lyophilized using Kinetics Flexi-Dry freeze-dryer. ESI-MS: m/z calcd for $C_{10}H_8N_2O_4S$ (M+H)$^+$ 253.26. found 252.85 (100%). $^1$H (d$_6$-DMSO) δ (ppm)=1.39 (t, J=7.0 Hz, 3H), 4.48 (q, J=7.0 Hz, 2H), 8.44 (m, 2H), 9.32 (s, 1H). $^{13}$C NMR (d$_6$-DMSO) δ (ppm)=13.8, 63.0, 120.1, 122.1, 125.5, 136.5, 145.9, 155.9, 159.3, 164.1.

Bernadi et al reported almost quantatative conversion of benzothiazole to ethyl 6-nitrobenzothiazole-2-carboxylate.[14] In this case, the low solubility of starting material 1 in aqueous $H_2SO_4$ limited the conversion to the desired product (~40% by TLC). The product 2 was also impossible to separate from the starting material 1 either by flash or gravity silica column chromatography.

Example 2

Synthesis of 6-nitrobenzothiazole-2-carboxamide (3)

6-Nitrobenzothiazole-2-carboxamide was synthesized from ethyl 6-nitrobenzothiazole-2-carboxylate according to the following reaction scheme.

In particular, crude ethyl 6-nitrobenzothiazole-2-carboxylate 2 (7.9 mmol, 2.0 g) was dissolved in 140 ml MeOH and purged with $NH_3$ gas. Conversion to the product was monitored by analytical TLC (3 Hexane: 2 EtOAc). Following complete conversion to the product (20 min) the solvent was removed in vacuo. The crude material was filtered with chloroform (30 ml) to yield a pale tan-colored solid (80% yield crude material). Agilent HPLC displayed partial conversion to the crude product 3 at 8.1 min. The compound 3 was used in the subsequent step without purification.

For analytical characterization, a small portion was purified by semi-preparative HPLC at 10 mL/min on a Waters preparative machine (Waters Symmetry prep C18, 7 μm, 19×300 mm column, photodiode array detection) with a linear gradient from 90% $H_2O$ (0.1% TFA) to 50% MeCN (0.1% TFA) for 30 min yielding a large product peak at 22.5 minutes. The fractions were collected and lyophilized using Kinetics Flexi-Dry freeze-dryer. ESI-MS: m/z calcd for $C_8H_5N_3O_3S$ (M+H)$^+$ 224.22. found 223.88 (100%). $^1$H (d$_6$-DMSO) δ (ppm)=8.30 (br s, NH), 8.31 (dd, J=9.0 Hz, J=0.5 Hz), 8.41 (dd, J=9.0 Hz, J=2.5 Hz), 8.65 (br s, NH), 9.28 (d, J=2.0 Hz). $^{13}$C NMR (d$_6$-DMSO) δ (ppm)=120.3, 122.1, 124.8, 137.1, 145.6, 156.6, 160.8, 171.1.

Example 3

Synthesis of 2-cyano-6-nitrobenzothiazole (4)

2-Cyano-6-nitrobenzothiazole was synthesized from 6-nitrobenzothiazole-2-carboxamide according to the following reaction scheme.

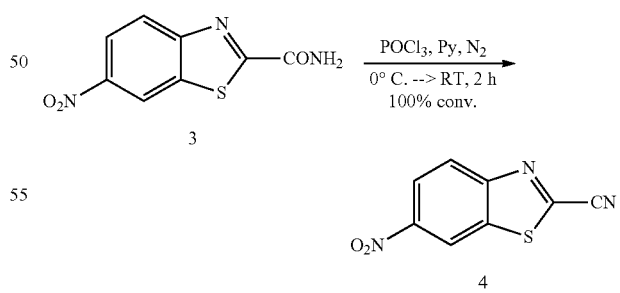

In particular, crude 6-nitrobenzothiazole-2-carboxamide 3 (4.5 mmol, 1.0 g), was dissolved in anhydrous pyridine (0.74 mol, 60 ml) and stirred at RT under $N_2$. The temperature of the reaction was dropped to 0° C. and $POCl_3$ (0.14 mol, 12.5 ml) was added dropwise to the reaction flask. After 20 min, the acetone/ice bath was removed and the reaction was stirred at RT for an additional 2 h. The contents were then transferred to a larger reaction flask containing 150 ml EtOAc at 0° C. While stifling, the reaction was quenched with the dropwise addition of water (150 ml).

The organic layer was separated, dried over $Na_2SO_4$, and concentrated in vacuo yielding an orange/brown solid material. TLC analysis (3 Hexane: 7 $CH_2Cl_2$) displayed 100% conversion to the product 4. Agilent HPLC displayed conversion to the crude product at 10.1 min. The product 4 was purified by gravity silica column chromatography (3 Hexane: 7 $CH_2Cl_2$) to yield a pale white solid (~24% pure product). ESI-MS: m/z calcd for $C_8H_3N_3O_2S$ (M+H)$^+$ 206.20. found 205.97 (100%). $^1H$ ($d_6$-DMSO): δ (ppm)=8.47 (s, 2H, 1H), 9.39 (s, 1H). $^{13}C$ NMR ($d_6$-DMSO): δ (ppm)=112.7, 120.3, 122.7, 125.3, 136.0, 143.2, 146.4, 154.6.

Example 4

Synthesis of 2-cyano-6-aminobenzothiazole (5)

2-Cyano-6-aminobenzothiazole was synthesized from 2-cyano-6-nitrobenzothiazole according to the following reaction scheme.

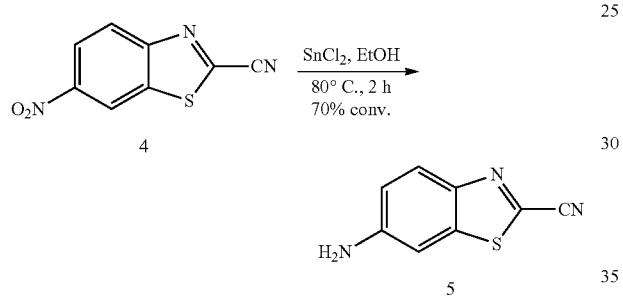

In particular, purified 2-cyano-6-nitrobenzothiazole 4 (0.49 mmol, 100 mg) was dissolved in 5 ml EtOH (200 Proof). 2.5 equivalents of $SnCl_2$ (1.3 mmol, 322 mg) was added to the flask. The reaction was heated to 60° C. under $N_2$, and stirred for 2 h. Over time the mixture changed from a bright fluorescent yellow to an orange/yellow coloring. After cooling to room temperature (RT), the reaction was poured into ice water (~5 ml) and the pH was adjusted using $NaHCO_3$ (pH 7).

The product 5 was extracted using EtOAc, dried over $MgSO_4$ and removed in vacuo (~65% yield). Agilent HPLC displayed conversion to the crude product at 7.4 min. The product 5 was purified by gravity silica column chromatography (3 Hexane: 2 EtOAc) to yield an orange/yellow solid. ESI-MS: m/z calcd for $C_8H_5N_3S$ (M+H)$^+$ 176.22. found 175.85 (100%). $^1H$ NMR ($d_6$-DMSO, 500 MHz) δ (ppm)= 6.15 and 6.55 (br s, $NH_2$), 6.97 (dd, J=9.0 Hz, J=2.0 Hz), 7.15 (d, J=2.5 Hz), 7.86 (d, J=9.0 Hz). $^{13}C$ NMR ($d_6$-DMSO) δ (ppm)=102.2, 114.1, 117.3, 125.0, 127.7, 138.2, 143.2, 150.4.

Example 5

Synthesis of ethyl 6-nitrobenzothiazole-2-carboxylate (7)

Ethyl 6-nitrobenzothiazole-2-carboxylate was synthesized from ethyl benzothiazole-2-carboxylate according to the following reaction scheme.

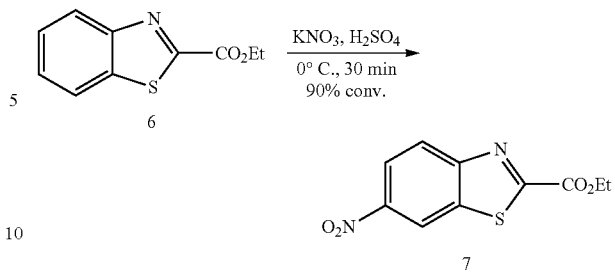

In particular, commercially available ethyl benzothiazole-2-carboxylate 6 (24.1 mmol, 5.0 g) was suspended in 22 ml conc. $H_2SO_4$ at 0° C. At 10° C. $KNO_3$ (26.4 mmol, 2.6 g) was added portionwise over 30 min to the stifling solution, not to exceed 15° C. Color of reaction changed from bright green/yellow to yellow over time. The reaction warmed from 25° C. to 40° C. for an additional 30 min. When the temperature of the reaction was decreased, the solution was poured over ice/water). The precipitate forming in solution was collected via glass frit vacuum filtration to yield a light yellow solid 7.

Resultant solid 7 was additionally washed with water, extracted into EtOAc, and concentrated in vacuo. Agilent HPLC displayed partial conversion to the crude product at ~10.0 min with a peak at ~9.9 min corresponding to the starting material. Attempts to purify the product were made using gravity silica column chromatography (4 Hexane: 1 EtOAc) to yield a yellow solid (~10% yield). Compound 7 was identified with LC/MS spectroscopic analysis as illustrated in FIG. 16-1, 16-2, and 16-3.

Example 6

Synthesis of benzothiazole-2-carboxamide (8)

Benzothiazole-2-carboxamide was synthesized from ethyl benzothiazole-2-carboxylate according to the following reaction scheme.

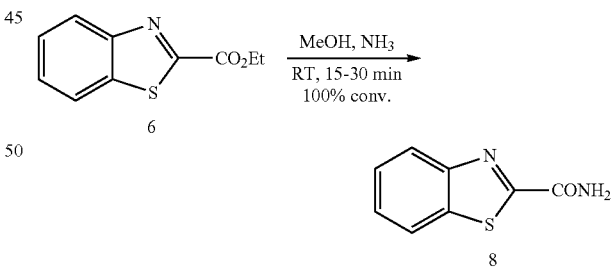

Figure 17A:
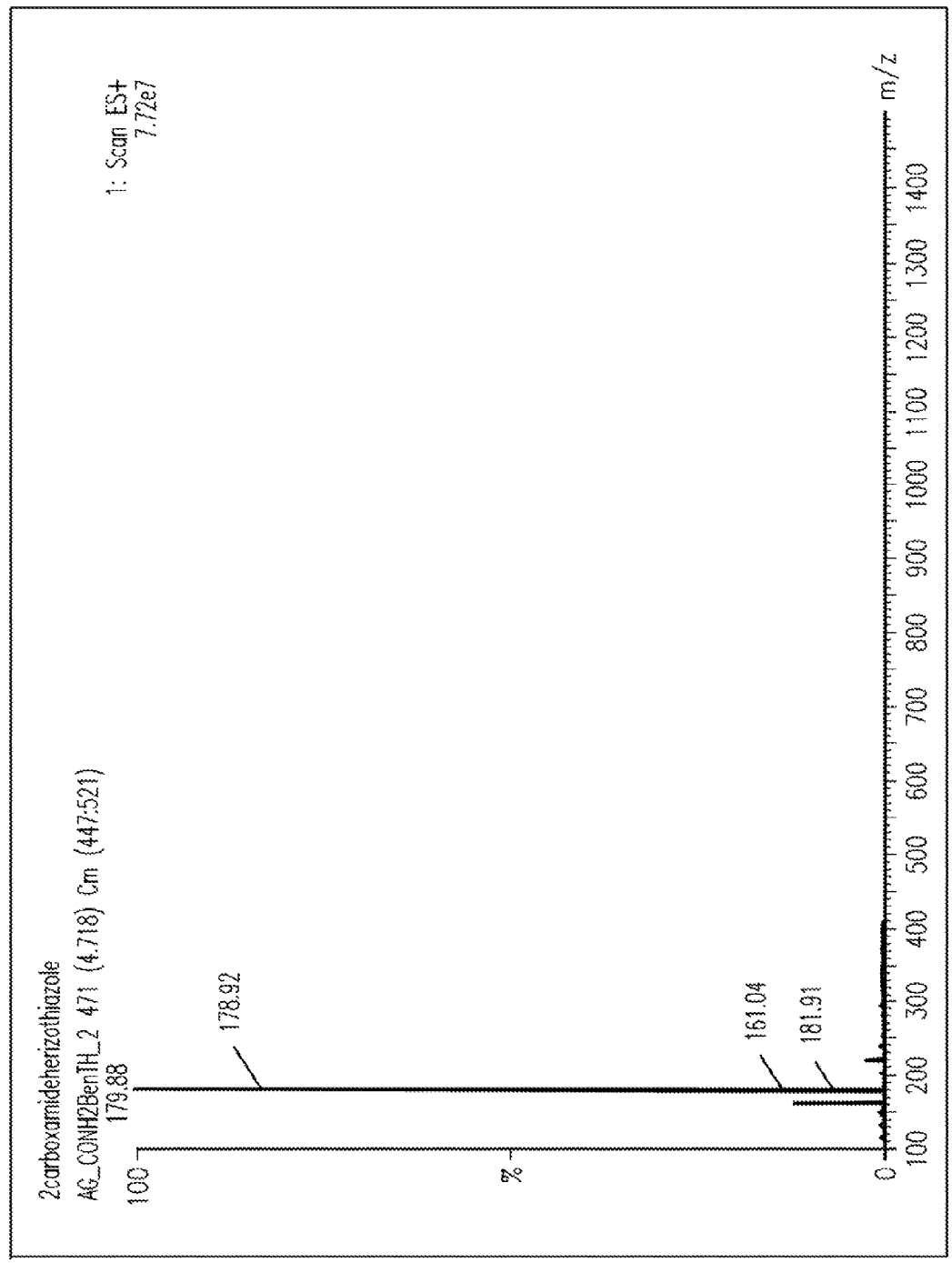
FIG. 17 shows liquid chromatography/mass spectrometry (FIG. 17A) and nuclear magnetic resonance spectra (FIG. 17B) for a compound according to an embodiment herein described.
Figure 17B:
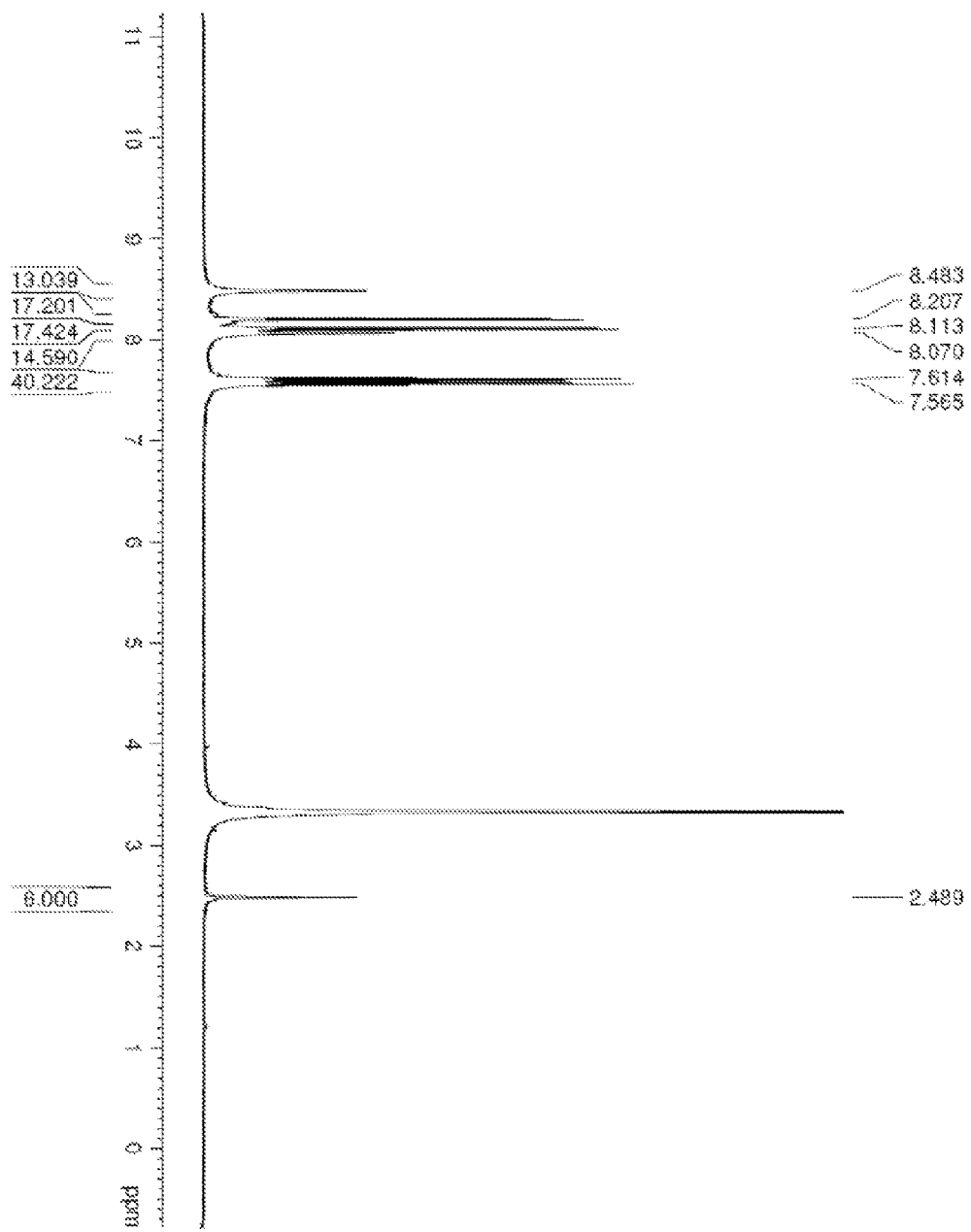

In particular, commercially available ethyl benzothiazole-2-carboxylate 6 (2.4 mmol, 0.5 g) was dissolved in 34 mL MeOH and purged with $NH_3$ gas. Conversion to the product was monitored by TLC (3 Hexane: 2 EtOAc). Following complete conversion to the product 8 (~30 min), the solvent was removed in vacuo. Agilent HPLC displayed 100% conversion to the desired product 8 with a single peak at ~8.0 min. The solid white compound was used in the subsequent step without purification. ESI-MS: m/z calcd for $C_8H_6N_2OS$ 179.02 (M+H)$^+$, 179.88 found (100%) (see LC/MS spectra of FIG. 17A and NMR spectra of FIG. 17B).

Example 7

Synthesis of 6-nitrobenzothiazole-2-carboxamide (9)

6-nitrobenzothiazole-2-carboxamide was synthesized from benzothiazole-2-carboxamide according to the following reaction scheme.

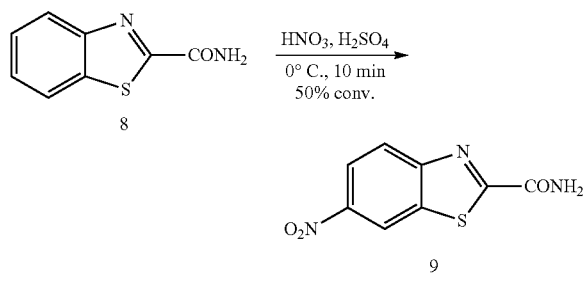

Figure 18:
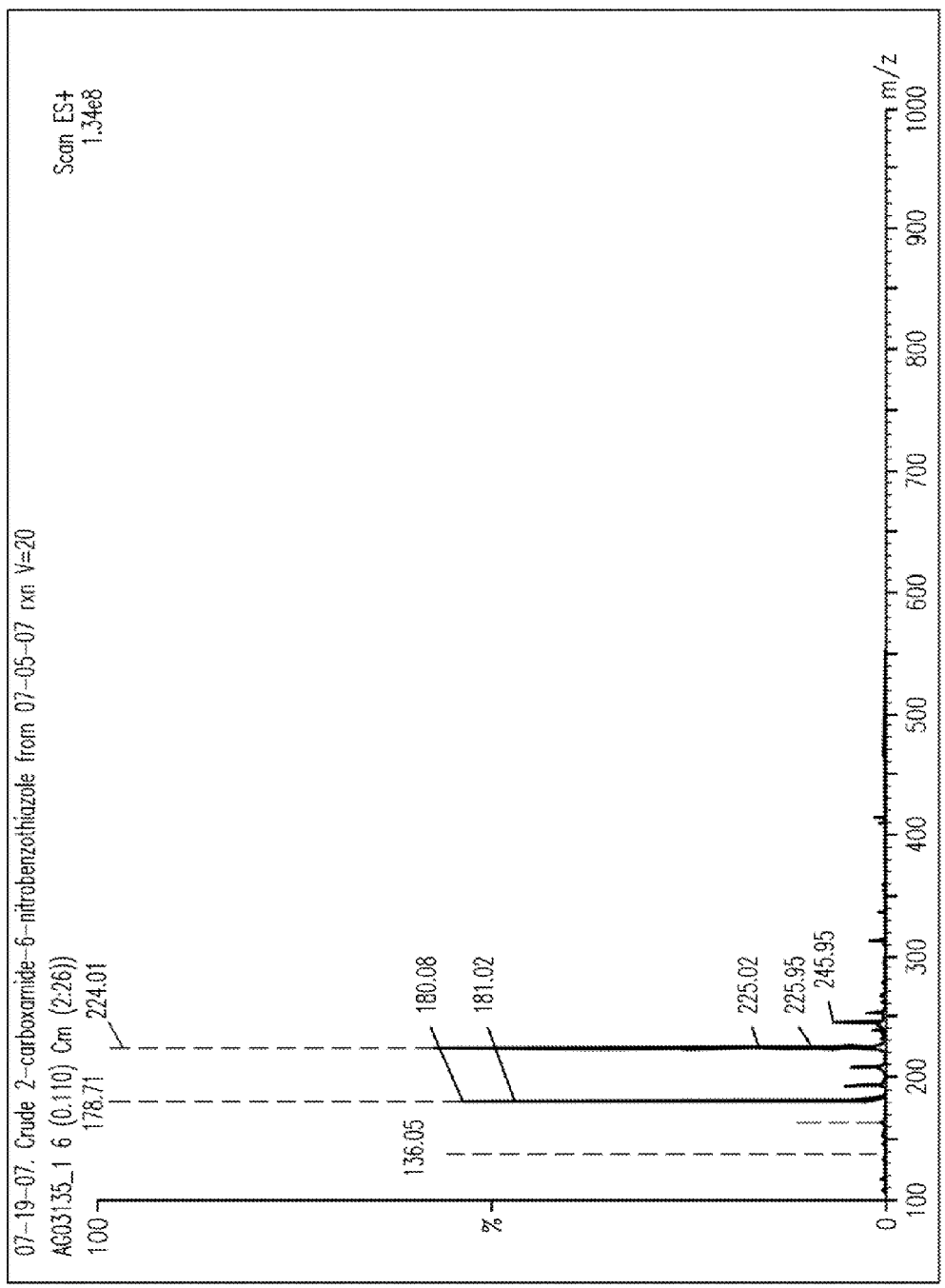
FIG. 18 shows liquid chromatography/mass spectrometry spectra for a compound according to an embodiment herein described.

In particular, 2-carboxamide-benzothiazole 8 (0.88 mmol, 0.156 g) was suspended in 0.655 ml conc. $H_2SO_4$ at 0° C. 1.3 equivalents of concentrated $HNO_3$ (1.1 mmol, 0.069 g) was added portionwise over 10 min to the stirring solution; not to exceed 0° C. The reaction remained at 0° C. for ~6 h and continued overnight; warming to 25° C. overnight. The following day the reaction was poured over ice/water forming a white precipitate in solution. The reaction was washed with water, extracted into EtOAc, and concentrated in vacuo to yield crude product. Attempts to purify the product were made using gravity silica column chromatography (Initially 3 Hexane: 7 $CH_2Cl_2$ followed by 3 Hexane: 2 EtOAc) to yield a pure white solid (~30% yield). (see LC/MS spectra of FIG. 18). Further NMR can be performed to detect the monofunctional benzothiazole comprising the $N_{O2}$ at position C6 versus thiazole substituted in the C4, C5, or C7 positions.

Example 8

Synthesis of 2-cyanobenzothiazole (10)

2-Cyanobenzothiazole was synthesized from benzothiazole-2-carboxamide according to the following reaction scheme.

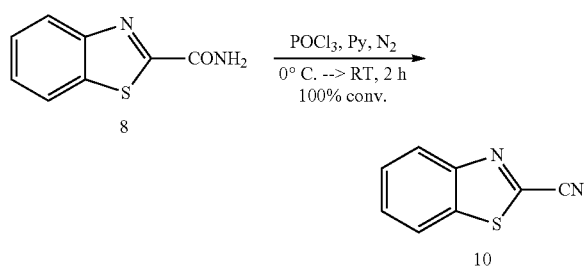

Figure 19A:
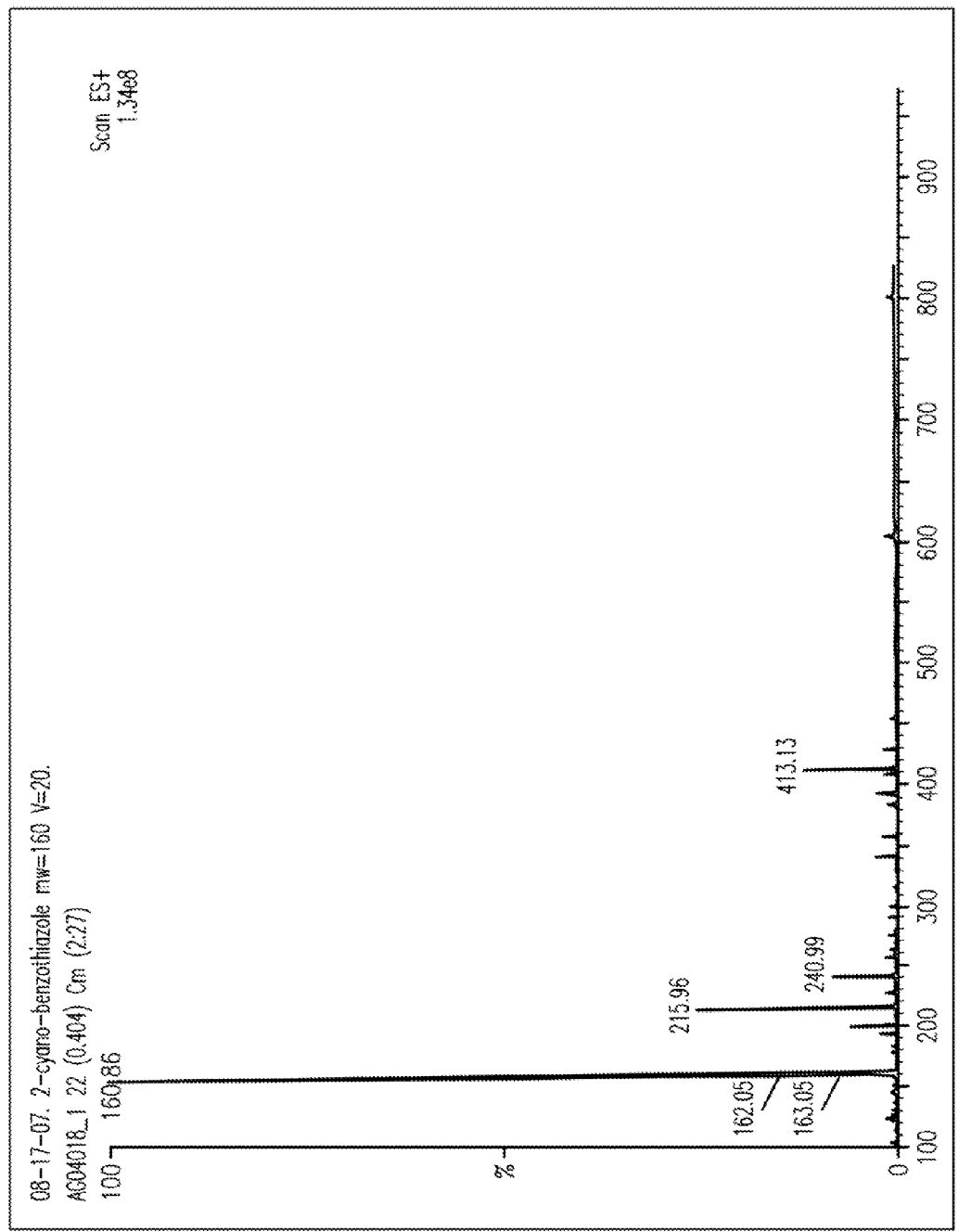
FIG. 19 shows liquid chromatography/mass spectrometry (FIG. 19A) and nuclear magnetic resonance spectra (FIG. 19B) for a compound according to an embodiment herein described.
Figure 19B:
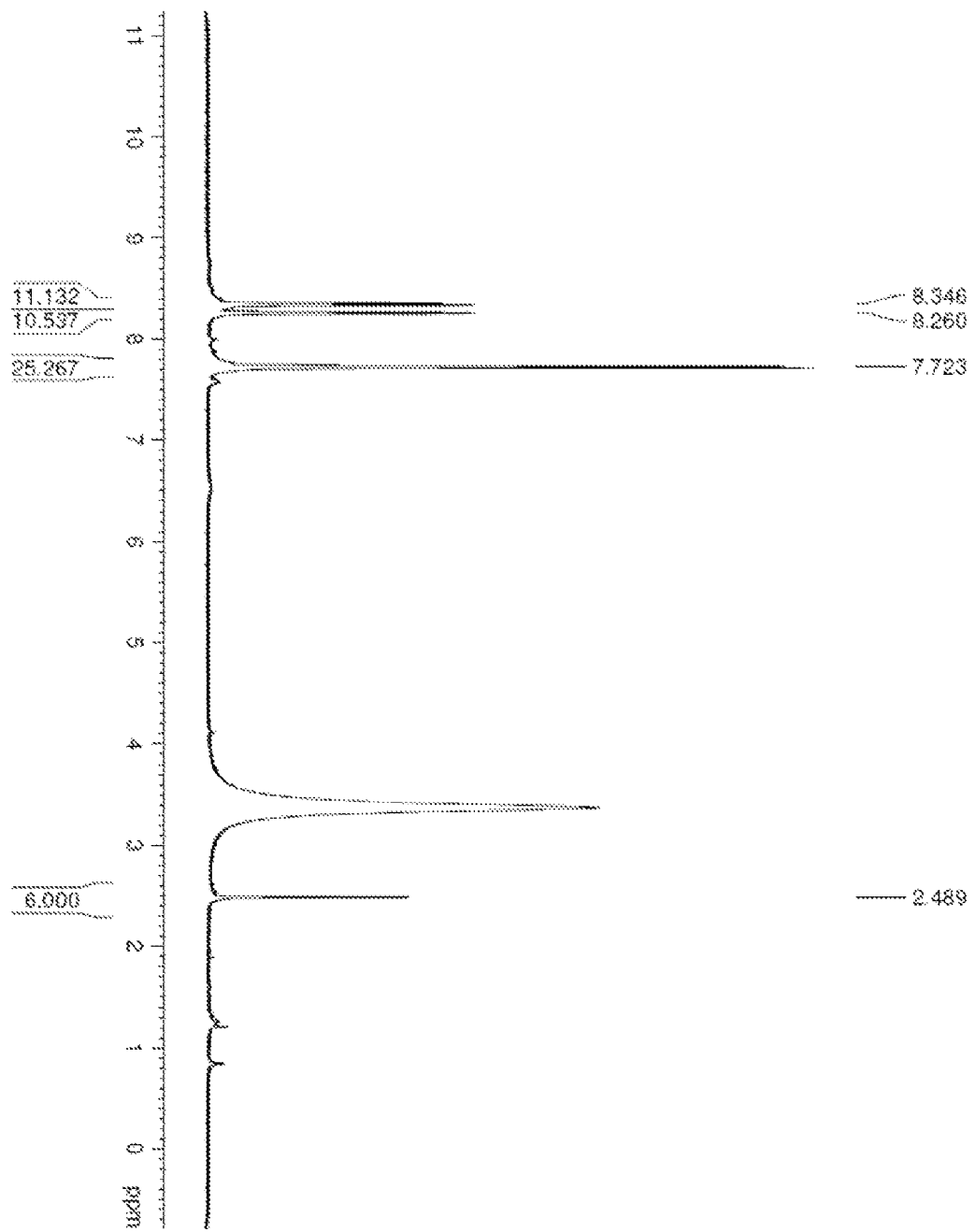

Benzothiazole-2-carboxamide 8 (0.61 mmol, 0.1 g) was dissolved in anhydrous pyridine (0.080 mol, 6.5 ml) and stirred under $N_2$ at 0° C. The temperature of the reaction was dropped to 0° C. during dropwise addition of $POCl_3$ (0.015 mol, 1.4 ml). The solution immediately changed from clear to a pale pink coloring with addition of $POCl_3$. After 20 min, the acetone/ice bath was removed and the reaction was stirred at RT for 2 h further. The tan/brown-colored reaction was then transferred to a larger reaction flask containing 10 ml EtOAc at 0° C. The reaction was quenched by the dropwise addition of water. The organic product 10 was washed with water, extracted with EtOAc, and concentrated in vacuo to yield a light yellow/orange product. TLC analysis (3 Hexane: 2 EtOAc) and Agilent HPLC displayed 100% conversion to the desired product (single peak at 10.5 min). The compound was used in the subsequent step without purification (95% yield). ESI-MS: m/z calcd for $C_8H_4N_2S$ 161.01 $(M+H)^+$, 160.86 found (100%). (see LC/MS spectra of FIG. 19A and NMR spectra of FIG. 19B).

Example 9

Synthesis of 2-cyano-6-nitrobenzothiazole (11)

2-Cyano-6-nitrobenzothiazole was synthesized from 2-cyanobenzothiazole according to the following reaction scheme.

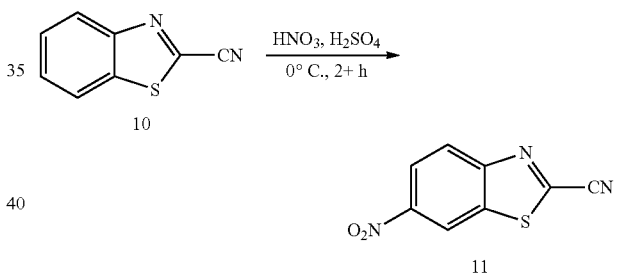

In particular 2-cyano-benzothiazole 10 (0.84 mmol, 0.134 g) was suspended in 0.563 ml conc. $H_2SO_4$ at 0° C. 1.3 equivalents of concentrated $HNO_3$ (1.1 mmol, 0.069 g) was added portionwise over 10 min to the stirring solution; not to exceed 0° C. over a total of ~45 min. The reaction proceeded further for 2 h and at 5 h the product was evident. The reaction was then poured over ice/water, extracted into EtOAc, and concentrated in vacuo to yield a crude yellow residue 11. For analytical characterization, a small portion was purified by semi-preparative HPLC at 10 mL/min on a Waters preparative machine (Waters Symmetry prep C18, 7 μm, 19×300 mm column, photodiode array detection) with a linear gradient from 90% $H_2O$ (0.1% TFA) to 50% MeCN (0.1% TFA) for 30 min yielding a large product peak at ~27 minutes. The fractions were collected and lyophilized using Kinetics Flexi-Dry freeze-dryer.

Further NMR can be performed to detect the monofunctional benzothiazole comprising the $NO_2$ at position C6 versus thiazole substituted in the C4, C5, or C7 positions.

Example 10

Synthesis of tyrosine-aminocyano derivative of 2-cyano-6-aminobenzothiazole

The tyrosine-aminocyano derivative of 2-cyano-6-aminobenzothiazole was synthesized according to the following reaction scheme.

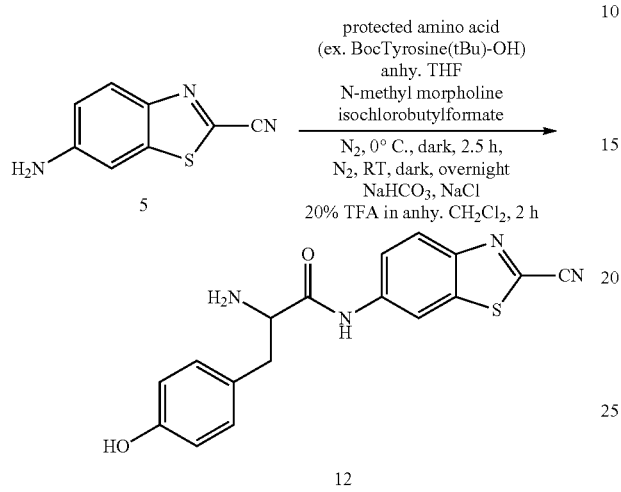

Tyrosine protected amino acid (0.32 mmoles, 0.11 g) was dissolved in 4 mL of anhydrous THF and stirred under $N_2$ at 0° C. in the dark. N-methylmorpholine (2 eq, 0.64 mmol, 0.070 mL) and isobutyl chloroformate (1.3 eq, 0.42 mmol, 0.055 mL) were added dropwise to the reaction at 0° C. and stirred for 30 min in the dark. Separately, purified 2-cyano-6-aminobenzothiazole 5 (0.32 mmol, 0.056 g) was dissolved in 1 mL of anhydrous THF and then added dropwise to the reaction flask over a period of 30 min. The reaction was stirred under $N_2$ in the dark at 0° C. for 2 h, followed by an overnight stir at room temperature in the dark. 24 h later the anhydrous THF was removed in vacuo. The product 12 was dissolved in EtOAc and washed with saturated $NaHCO_3$ and NaCl to quench any remaining isobutyl chloroformate. The organic layer was collected, dried with $MgSO_4$, and evaporated to dryness. The protected group on the tyrosine portion of the product was removed using 20% TFA in anhydrous $CH_2Cl_2$; stirred at room temperature in the dark for 2 h. Following deprotection, the product 12 was evaporated to dryness and placed on vacuum.

Figure 20:
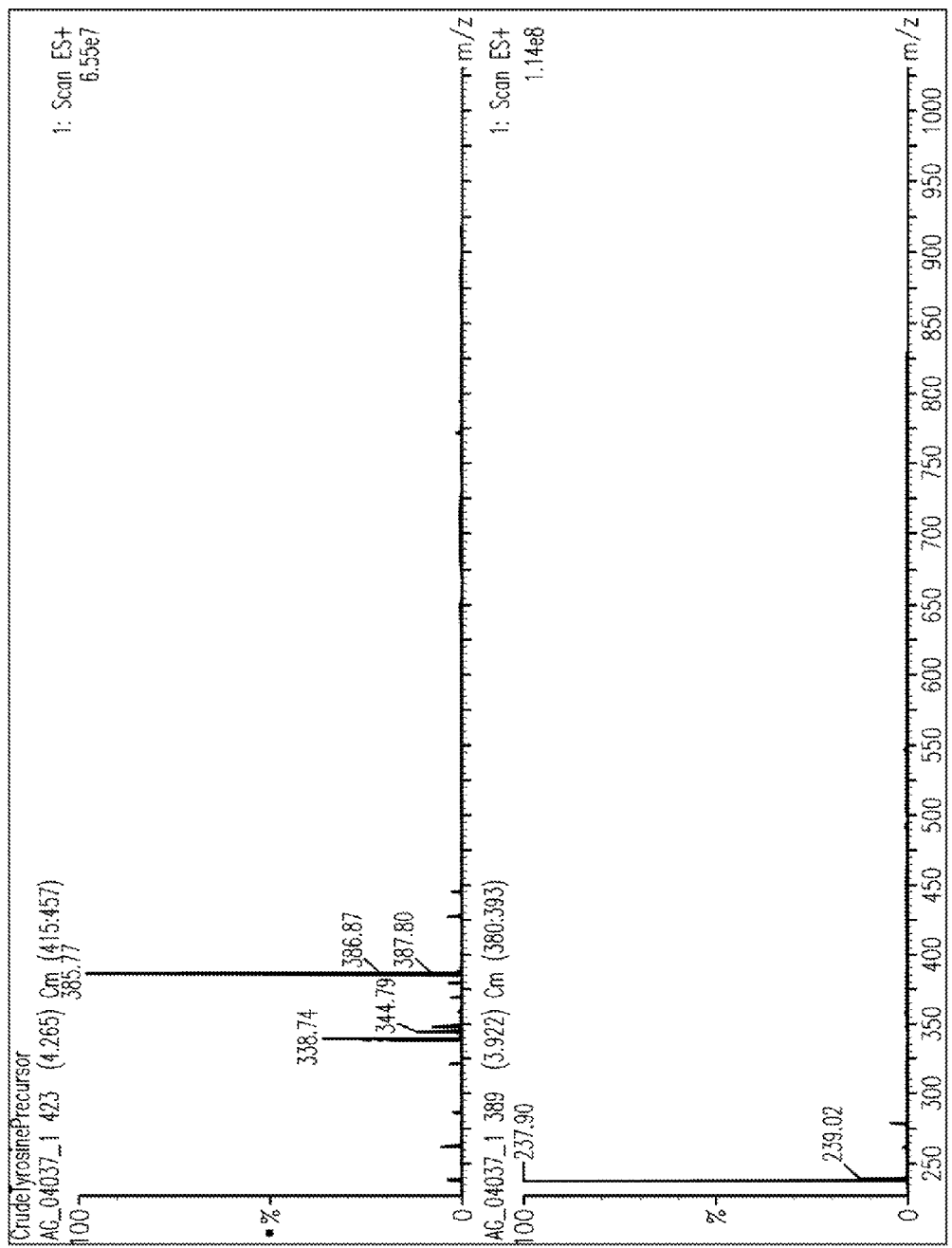
FIG. 20 shows liquid chromatography/mass spectrometry spectra for a compound according to an embodiment herein described.

The residue was redissolved in 50/50 0.1% TFA in MeCN & $H_2O$ (+drops of DMF to solubilize) and any solid residue removed by filtration through a 0.45 μm filter. Analytical HPLC with a linear gradient from 95% $H_2O$ (0.1% TFA) to 80% MeCN (0.1% TFA) over 15 min yielded a peak at 7.3 min. The material was purified using the semi-preparative HPLC at 10 mL/min on a Waters preparative machine (Waters Symmetry prep C18, 7 μm, 19×300 mm column, photodiode array detection) with a linear gradient from 90% $H_2O$ (0.1% TFA) to 50% MeCN (0.1% TFA) for 30 min. Semi-preparative HPLC fractions at 17 min were collected and lyophilized using Kinetics Flexi-Dry freeze-dryer. Compound 12 was identified with LC/MS spectroscopic analysis as illustrated in FIG. 20.

This same procedure can be applied for various other amino acids (e.g. the 20 amino acids) as a means to develop new conjugates as bioluminescence probes that may vary in their kinetic activity (pharmacodynamics/pharmacokinetics) in vitro and in vivo

Example 11

Synthesis of tyrosine-D-aminoluciferin from amino acid-conjugated 2-cyano-6-aminobenzothiazole intermediate The tyrosine-d-aminoluciferin compound was synthesized according to the following reaction scheme

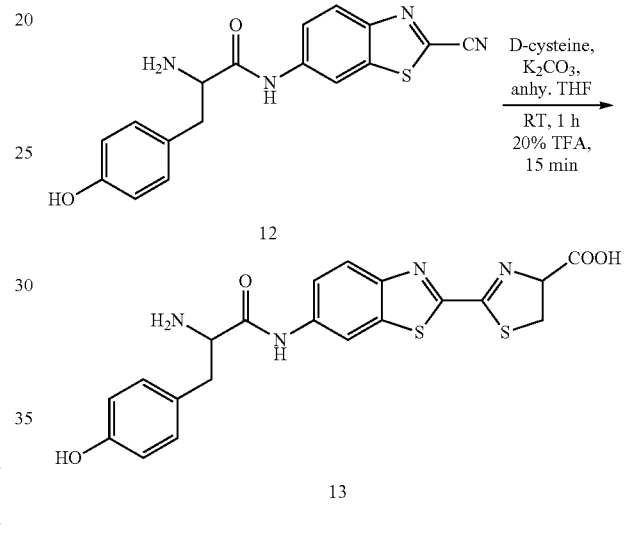

The deprotected and purified amino acid-conjugated 2-cyano-6-aminobenzothiazole (e.g. tyrosine conjugated; 0.048 mmoles, 0.024 g) was dissolved in anhydrous THF (0.5 mL), followed by dropwise addition of D-cysteine (1.2 eq, 0.06 mmoles, 0.011 g, in 0.056 mL; adjusted to pH 8) while stifling the reaction at RT in the dark for 2 h. After 2 h, the reaction was evaporated to dryness and placed on vacuum. The residue was re-dissolved in a mixture of anhy. THF and any solid residue removed by filtration through a 0.45 μm filter. The solvents were removed in vacuo.

Example 12

Synthesis of peptide conjugated 2-cyano-6-aminoacid-aminobenzothiazole from the amino acid-conjugated 2-cyano-6-aminobenzothiazole intermediate The peptide-conjugated 2-cyano-6-aminoacid-aminobenzothiazole was synthesized according to the following reaction scheme.

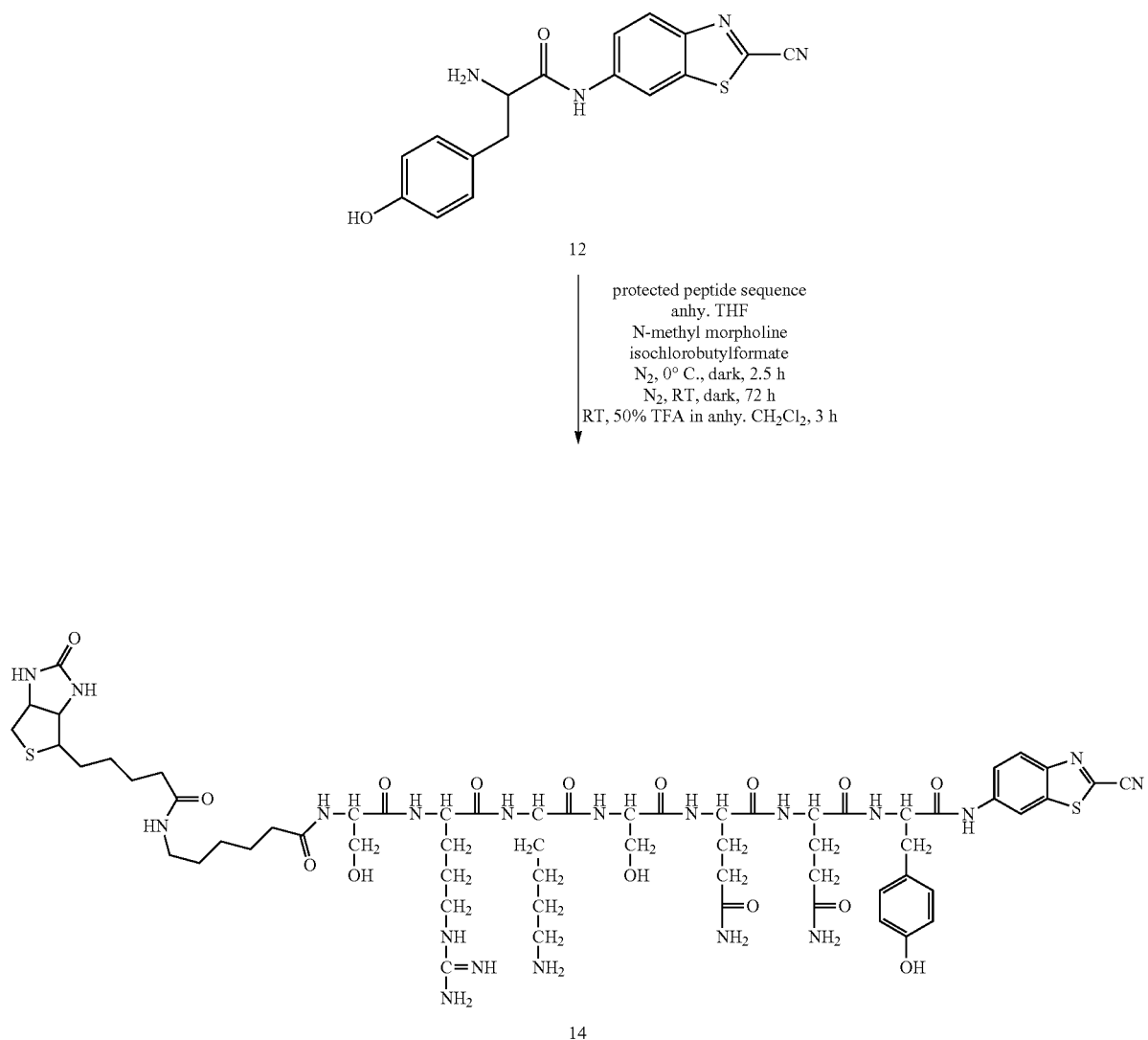

Figure 21:
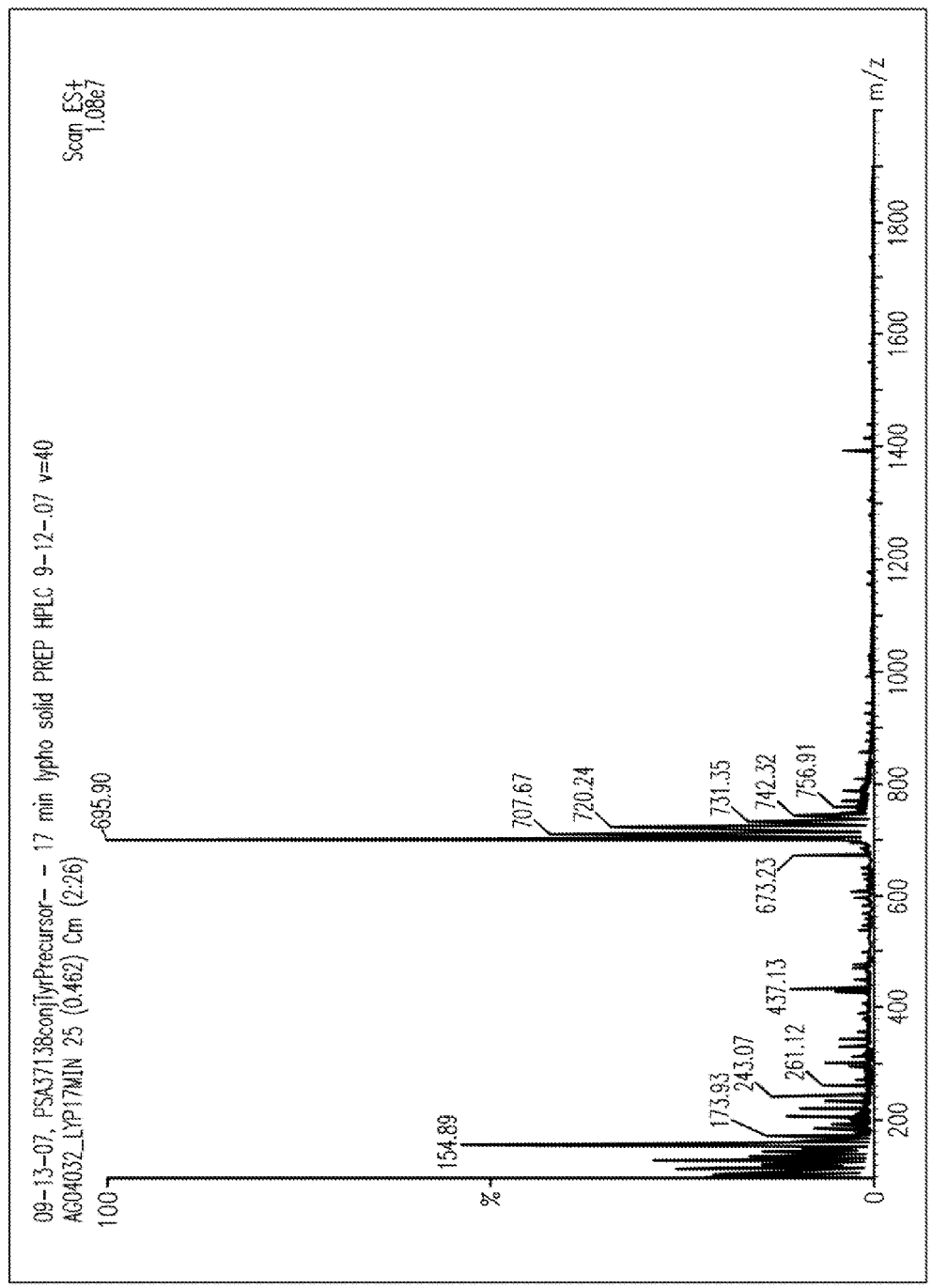
FIG. 21 shows liquid chromatography/mass spectrometry spectra for a compound according to an embodiment herein described.

The peptide sequence was designed to be recognized by a specific protease in the blood that is indicative of disease (e.g. prostate specific antigen (PSA), which correlates to prostate cancer; a wide variety of proteases are also present and these levels may change in response to biological insults conferred by infection, malignant growth and autoimmune responses[16]. The protected peptide sequence (0.033 mmoles, 0.067 g) was dissolved in 2.3 mL of anhydrous THF (+small amount of anhydrous DMF), sonicated, and stirred under $N_2$ at 0° C. in the dark (material in suspension). N-methylmorpholine (2 eq, 0.07 mmol, 0.007 mL) and isobutyl chloroformate (1.3 eq, 0.04 mmol, 0.006 mL) were added drop-wise to the reaction at 0° C. and stirred for 30 min in the dark. Separately, purified amino acid-conjugated 2-cyano-6-aminobenzothiazole (e.g. tyrosine conjugated) 12 (0.03 mmol, 0.011 g) was dissolved in 0.2 mL of anhydrous THF and then added dropwise to the reaction flask over a period of 30 min. The reaction was stirred under $N_2$ in the dark at 0° C. for 2 h, followed by a 72 h stir at room temperature in the dark. After 72 h, the anhydrous THF/DMF was removed in vacuo. The product 14 was dissolved in EtOAc and washed with saturated $NaHCO_3$ to quench any remaining isobutyl chloroformate. The organic layer was collected and evaporated to dryness to yield a bright yellow to golden orange/yellow residue. The protected group on the peptide portion of the product was removed using 50% TFA in anhydrous $CH_2Cl_2$; stirred at RT in the dark for 3 h. Following deprotection, the product 14 was evaporated to dryness and placed on vacuum. Compound 14 was identified with LC/MS spectroscopic analysis as illustrated in FIG. 21.

This same procedure can be applied for various other peptide sequences as a means to develop new conjugates as bioluminescence probes for detection of various other proteases that link to disease.

Example 13

Synthesis of peptide conjugated tyrosine-D-aminoluciferin from the peptide conjugated 2-cyano-6-aminobenzothiazole-tyrosine-conjugated intermediate The peptide-conjugated tyrosine-D-aminoluciferin was synthesized according to the following reaction scheme.

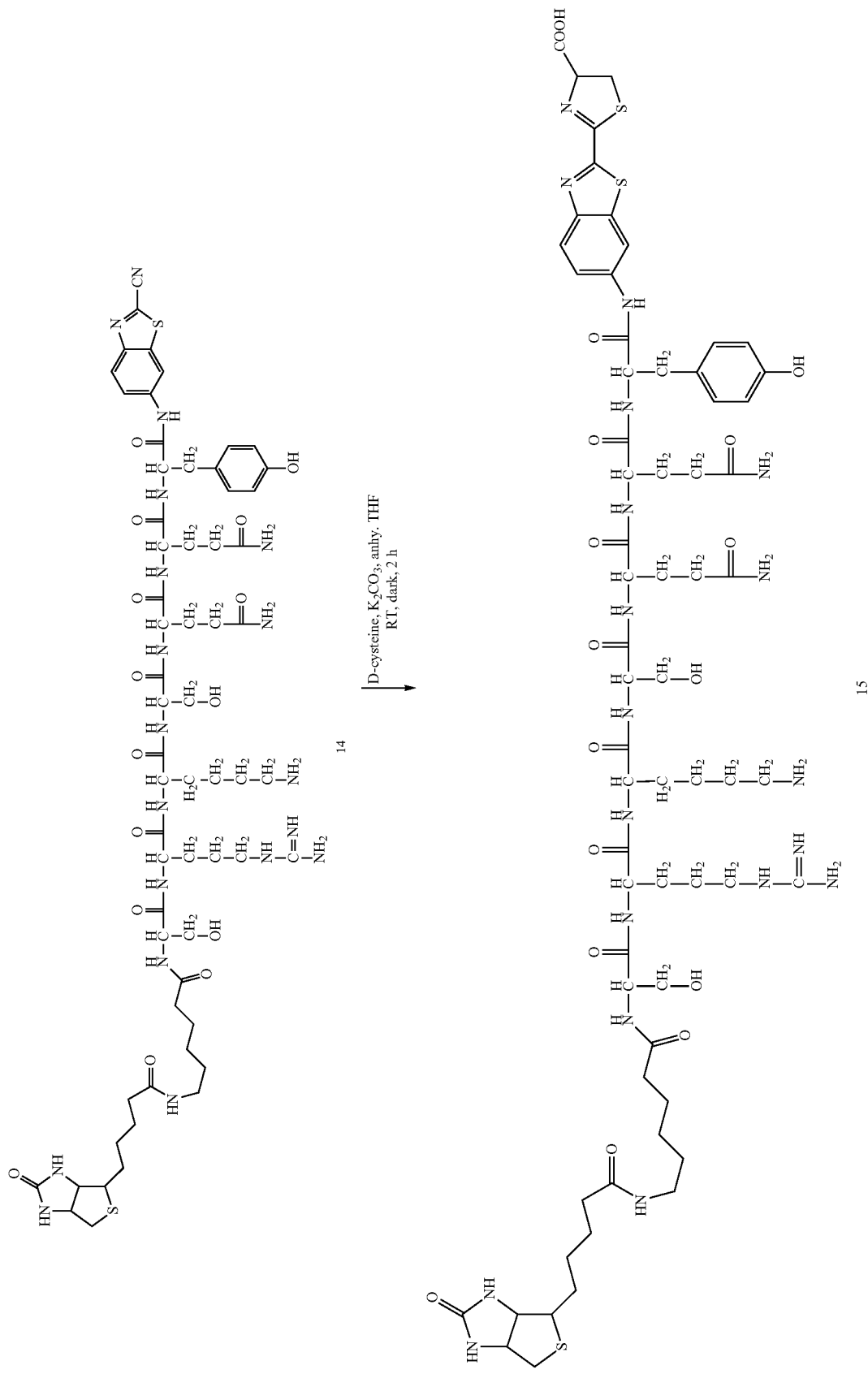

The deprotected and purified peptide-conjugated 2-cyano-6-aminobenzothiazole-[amino acid] (0.006 mmoles, 0.008 g) was dissolved in anhydrous THF (0.01 mL), followed by drop-wise addition of D-cysteine (1.2 eq, 0.007 mmoles, 0.001 g, 0.001 mL) while stifling the reaction at RT in the dark for 2 h. After 2 h, the reaction was evaporated to dryness and placed on vacuum. The residue was re-dissolved in a mixture of anhy. THF and any solid residue removed by filtration through a 0.45 μm filter. The THF was removed in vacuo Example 14

Synthesis of a Carboxylate-Modified Luciferin Amino Acid/Peptide Probe

Chlorotrityl chloride (CTC) resin can be used to synthesize amino acid/peptide derivatives of D-Luciferin as outlined below. An example for phenylalanine is shown below however chlorotryl chloride resin is commonly used to synthesize peptides, A peptide of any length can be synthesized using standard Fmoc amino acid synthesis the D-luciferin can be conjugated as a last step and the conjugate cleaved from the resin. Purification is using reversed phase high performance liquid chromatography (HPLC)

Figure 14:
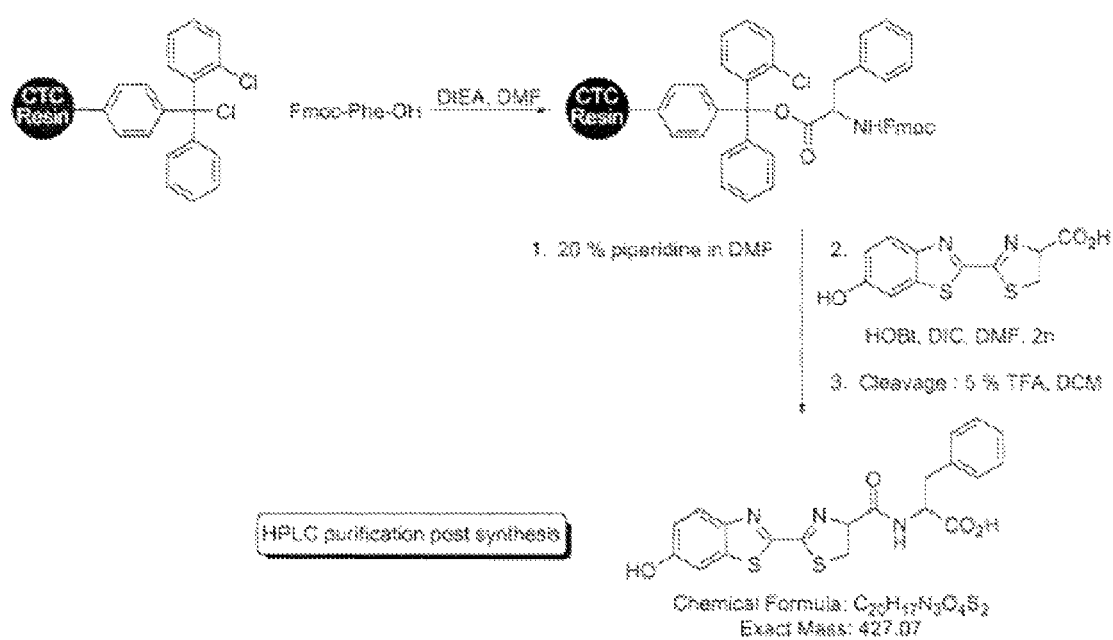
FIG. 14 shows a schematic representation of a method to provide a carboxylate modified luciferin amino acid/peptide probes according to an embodiment herein described.

Reference is made to the reaction Scheme of FIG. 14 showing a schematic illustration of an exemplary reaction scheme.

Example 14

Methods Using a Carboxylate-Modified Luciferin Amino Acid/Peptide Probe

Figure 15A:
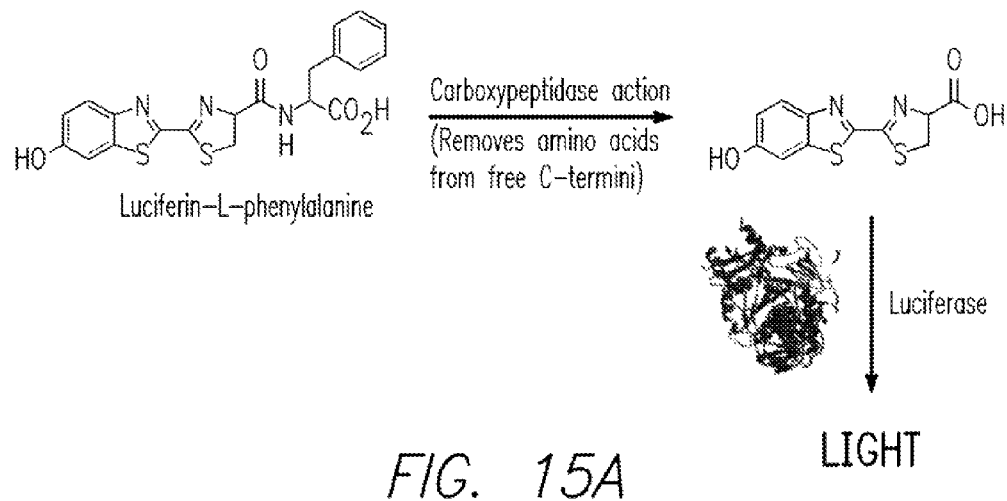
FIG. 15 shows a schematic representation of a method using a carboxylate modified luciferin amino acid/peptide probes according to an embodiment herein described.

Carboxypeptidase Y was used but other carboxypeptidases are expected to be suitable depending on the nature of the amino acids attached to the D-luciferin as will be understood by a skilled person. Carboxypeptidase Y (sold supported or free in solution) can be used to remove C-termini amino acids from a peptide. In the case shown here, it will remove phenylalanine from the conjugate, releasing the D-luciferin for reaction with the enzyme. Carboxypeptidase Y is expected to be confirmed as functioning optimally using hippuryl-L-phenylalanine, a commercially available UV-active substrate for carboxypeptidases. Reference is made to the reaction The scheme of FIG. 15A showing a schematic illustration of an exemplary reaction scheme.

Figure 15B:
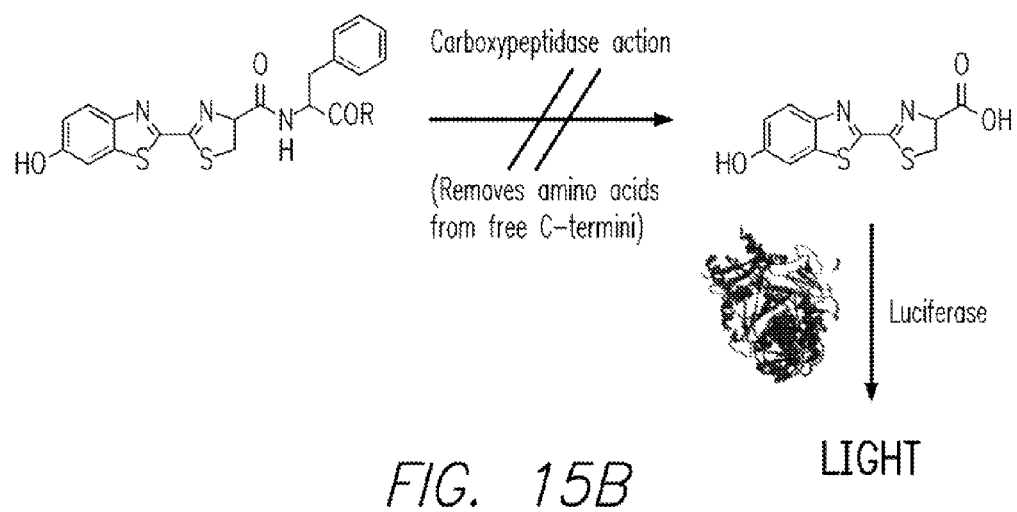
Figure 15C:
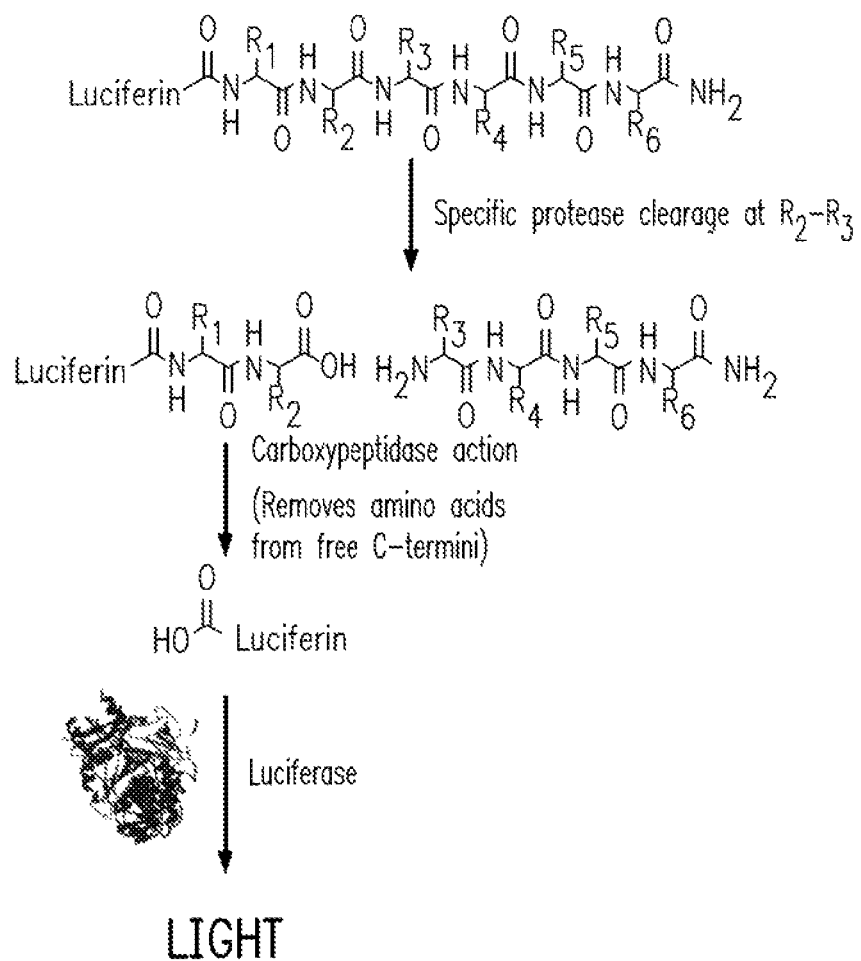
Figures 1, 16:
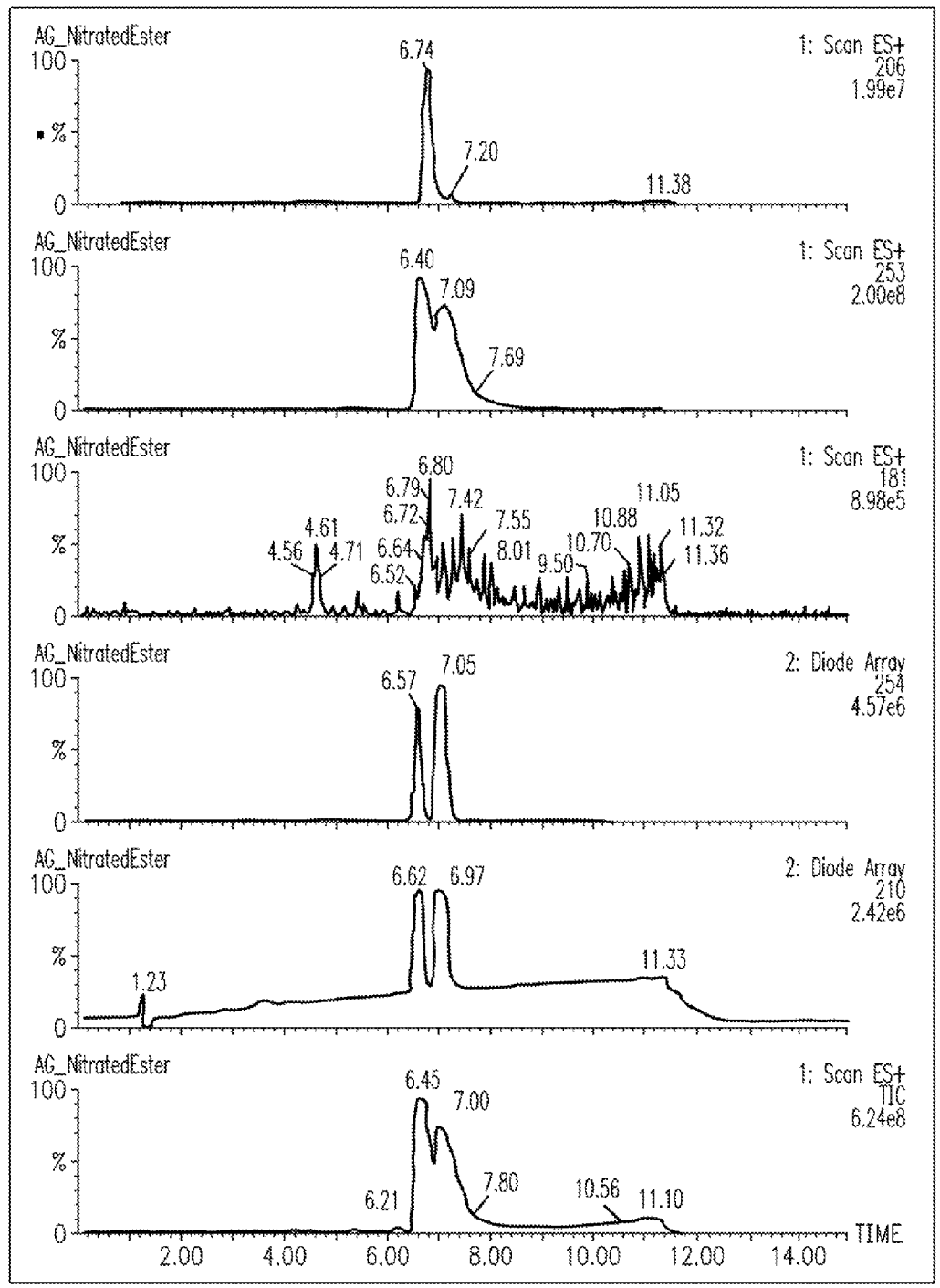
Figures 2, 16:
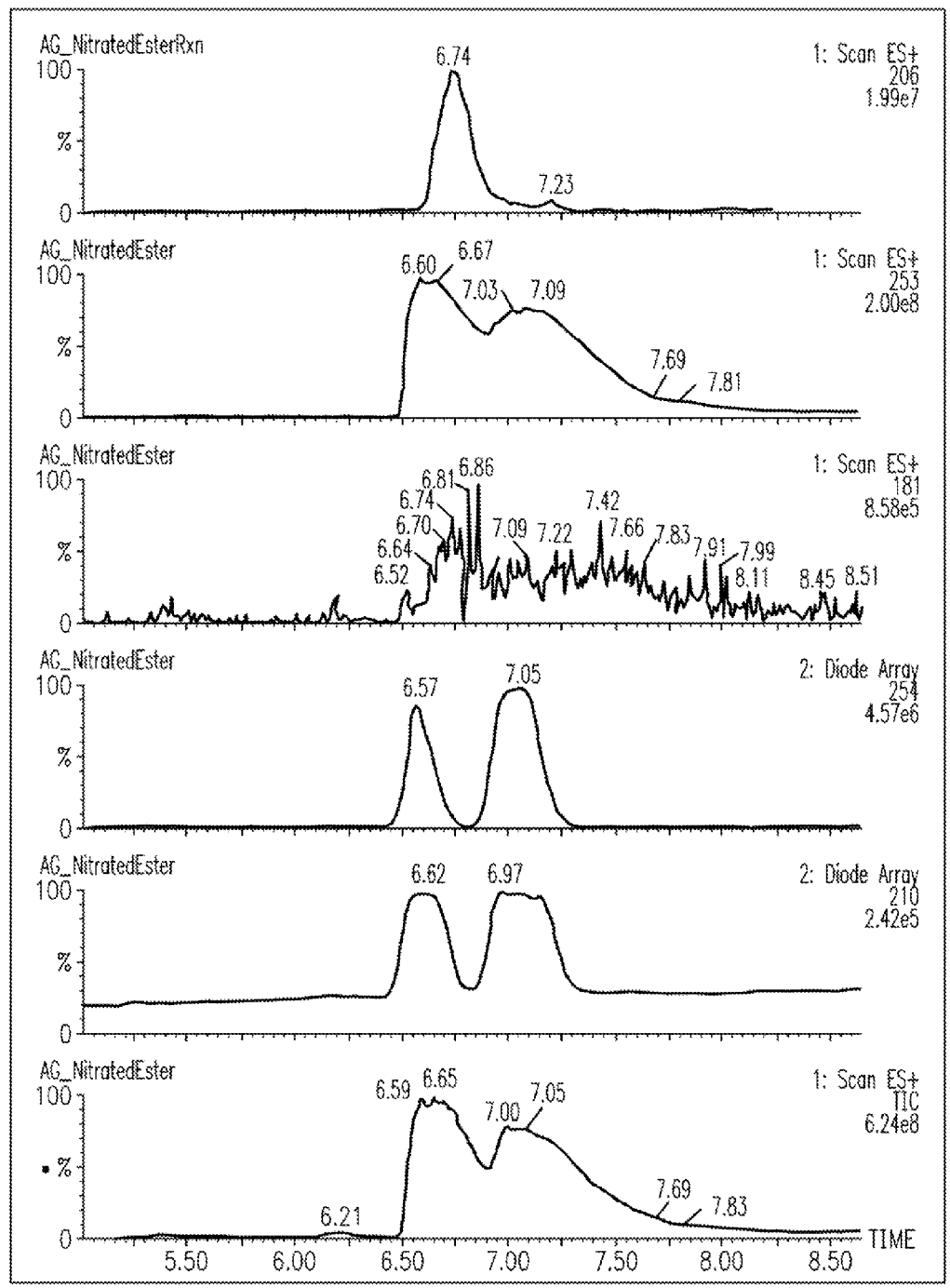
Figures 3, 16:
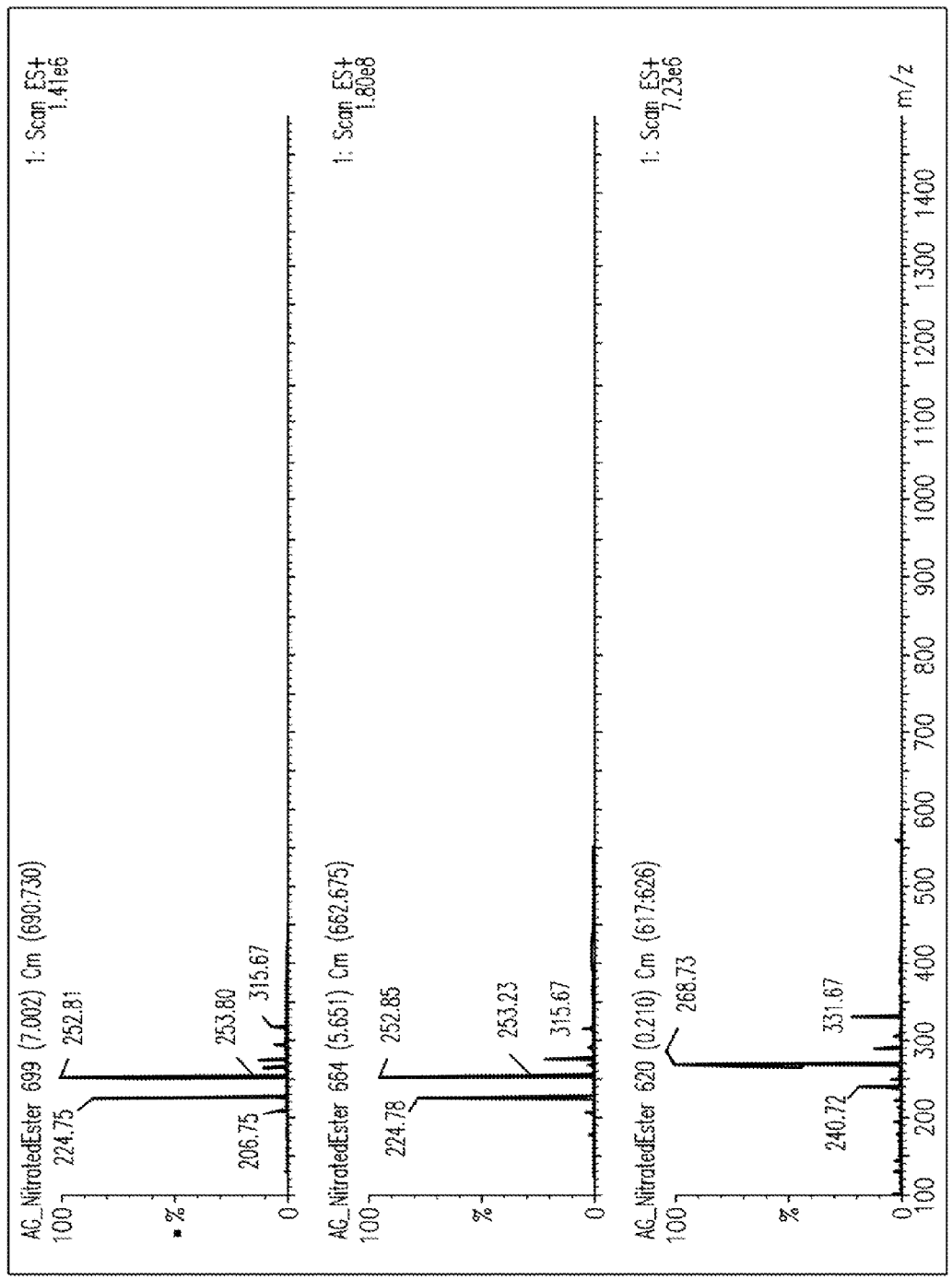

A blocking carboxypeptidase activity using a blocking agent (e.g. CONH2) on the C-terminus of the conjugates was investigated as outlined in FIG. 15 B.

These determinations are expected to confirm the utility of D-luciferin . . . amino acid I peptide conjugates as extremely sensitive probes for proteolytic action for in vitro and in vivo assays as outlined below. This example shows the C terminus of the substrate blocked as a carboxamide. Only upon proteolytic cleavage of the probe will free carboxy terminus be revealed for the carboxypeptidase to digest and release the D-luciferin for subsequent reaction with luciferase. In this connection reference is made to the schematic illustration of FIG. 15 C.

The examples set forth above are provided to give those of ordinary skill in the art a complete disclosure and description of how to make and use the embodiments of the compounds, compositions, systems and methods of the disclosure, and are not intended to limit the scope of what the inventors regard as their disclosure. All patents and publications mentioned in the specification are indicative of the levels of skill of those skilled in the art to which the disclosure pertains.

The entire disclosure of each document cited (including patents, patent applications, journal articles, abstracts, laboratory manuals, books, or other disclosures) in the Background, Summary, Detailed Description, and Examples is hereby incorporated herein by reference. All references cited in this disclosure are incorporated by reference to the same extent as if each reference had been incorporated by reference in its entirety individually.

It is to be understood that the disclosures are not limited to particular compositions or biological systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

When a Markush group or other grouping is used herein, all individual members of the group and all combinations and possible subcombinations of the group are intended to be individually included in the disclosure. Every combination of components or materials described or exemplified herein can be used to practice the disclosure, unless otherwise stated. One of ordinary skill in the art will appreciate that methods, device elements, and materials other than those specifically exemplified can be employed in the practice of the disclosure without resort to undue experimentation. All art-known functional equivalents, of any such methods, device elements, and materials are intended to be included in this disclosure. Whenever a range is given in the specification, for example, a temperature range, a frequency range, a time range, or a composition range, all intermediate ranges and all subranges, as well as, all individual values included in the ranges given are intended to be included in the disclosure. Any one or more individual members of a range or group disclosed herein can be excluded from a claim of this disclosure. The disclosure illustratively described herein suitably can be practiced in the absence of any element or elements, limitation or limitations which is not specifically disclosed herein.

A number of embodiments of the disclosure have been described. The specific embodiments provided herein are examples of useful embodiments of the disclosure and it will be apparent to one skilled in the art that the disclosure can be carried out using a large number of variations of the monofunctional benzothiazoles, compositions, methods steps, and systems set forth in the present description. As will be obvious to one of skill in the art, methods and devices useful for the present methods can include a large number of optional composition and processing elements and steps.

It will be understood that various modifications may be made without departing from the spirit and scope of the present disclosure. Accordingly, other embodiments are within the scope of the following claims.

REFERENCES (1) Ignowski, J. M.; Schaffer, D. V. *Biotechnol. Bioeng.* 2004, 86, 827-34.
(2) Hsieh, C.; Zie, Z.; Yu, J.; Martin, W. D.; Datta, M. W.; Wu, G.; Chung, L. W. K. *The Prostate* 2007, 67, 685-691.
(3) Lee, K. C.; Hamstra, D. A.; Bhojani, M. S.; Khan, A. P.; Ross, B. D.; Rehemtulla, A. *Clin. Cancer Res.* 2007, 13, 1839-1846.

(4) Contag, C. H.; Contag, P. R.; Mullins, J. I.; Spilman, S. D.; Stevenson, D. K.; Benaron, D. A. *Mol. Microbiol.* 1995, 18, 593-603.
(5) O'Brien, M. A.; Daily, W. J.; Hesselberth, P. E.; Moravec, R. A.; Scurria, M. A.; Klaubert, D. H.; Bulleit, R. F.; Wood, K. V. *J. Biomol. Screen.* 2005, 10, 137-148.
(6) Cali, J. J.; Ma, D.; Solbol, M.; Good, T.; Liu, D. *Promega Cell Notes* 2006, 14, 20-24.
(7) Deluca, M. *Adv. Enzymol. Relat. Areas Mol. Biol.* 1976, 44, 37-68.
(8) Seliger, H. H.; Mc, E. W. *Arch. Biochem. Biophys.* 1960, 88, 136-41.
(9) Koo, J. A.; Schmidt, S. P.; Schuster, G. B. *Proc Natl Acad Sci USA* 1978, 75, 30-3.
(10) White, E. H.; Woerther, H.; Selinger, H. H.; McElroy, W. D. *J. Am. Chem. Soc.* 1966, 88, 2015-2019.
(11) Monsees, T.; Miska, W.; Geiger, R. *Anal. Biochem.* 1994, 221, 329-334.
(12) Katz, L. *J. Am. Chem. Soc.* 1951, 73, 4007-4010.
(13) Shinde, R. R.; Perkins, J.; Contag, C. H. *Biochemistry* 2006, 45, 11103-11112.
(14) Bernardi, R.; Caronna, T.; Minisci, F.; Perchinunno, M. *Tetrahedron Lett.* 1973, 9
(15) Electrophilic cyanations. II. Synthesis of heteroarenecarbonitriles by electrophilic cyanation; reactionmetalated heteroarenes with p-toluenesulfonyl cyanide. Nagasaki, Izuru et al. Heterocycles, 46, 443-450, 1997.
(16) J Jacobs et al. J Proteome Research, 4, 1073-85 (2005).
(17) Journal of Chemical Research, Synopses, (4), 152-3; 1995
(18) Indian Journal of Chemistry, Section B: Organic Chemistry Including Medicinal Chemistry, 15B(2), 121-4; 1977.
(19) Journal of Chemical Research, (7), 474-476; 2004 (20) Journal fuer Praktische Chemie (Leipzig), 331(2), 243-62; 1989

What is claimed is:
1. A method to provide 2-cyano-6-aminobenzothiazole from a monofunctional benzothiazole, the method comprising:
providing the monofunctional benzothiazole ethyl benzothiazole-2-carboxylate and introducing a nitro group to position C6 of the ethyl benzothiazole-2-carboxylate;
attaching in position C2 a functional group of formula (I) (C(=$X_1$)NH2) wherein $X_1$ is O; and
converting the functional group of formula (I) to a cyanide group through dehydration of the C(=O)NH2 group;
and reducing the nitro group in C6 to provide 2-cyano-6-aminobenzothiazole.
2. A method to provide 2-cyano-6-aminobenzothiazole from a monofunctional benzothiazole, the method comprising
providing a monofunctional benzothiazole selected from the group consisting of ethyl-6-nitrobenzothiazole-2-carboxylate and a ethyl benzothiazole-2-carboxylate;
converting the C2 functional group into an amide of formula (I) (C(=$X_1$)$NH_2$) wherein $X_1$ is O; and
converting the amide of formula (I) to a cyanide group, through elimination of a $H_2X_1$ compound,
wherein the monofunctional benzothiazole either comprises an amino group in position C6 or is modified to comprise an amino group in position C6.
3. The method of claim 2 wherein the converting of the C2 functional group into an amide of formula (I) is performed by reacting the monofunctional benzothiazole with an amine.
4. The method of claim 3, wherein converting the amide of formula (I) to a cyanide group, is performed by dehydration of the C(=O)NH2 group.

* * * * *